US006429362B1

(12) United States Patent
Crane

(10) Patent No.: US 6,429,362 B1
(45) Date of Patent: Aug. 6, 2002

(54) MAIZE PR-1 GENE PROMOTERS

(75) Inventor: Virginia C. Crane, Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/257,583

(22) Filed: Feb. 25, 1999

Related U.S. Application Data

(60) Provisional application No. 60/076,100, filed on Feb. 26, 1998, and provisional application No. 60/079,648, filed on Mar. 27, 1998.

(51) Int. Cl.⁷ ................................................. A01H 5/00
(52) U.S. Cl. ............................... 800/320.1; 435/320.1; 435/412; 435/419; 536/24.1; 800/278; 800/298
(58) Field of Search ..................... 536/24.1; 435/69.1, 435/320.1, 419, 468; 800/278, 298, 320.1

(56) References Cited

FOREIGN PATENT DOCUMENTS

| EP | 307 841 A1 | 3/1989 |
|---|---|---|
| WO | WO 89/02437 | 3/1989 |
| WO | WO 95/19443 | 7/1995 |
| WO | WO 98/03536 | 1/1998 |

OTHER PUBLICATIONS

Benfey PN, et al. "The cauliflower mosaic virus 35S promoter: Combinatorial regulation of transcription in plants." Science 250: 959–966, Nov. 1990.*
Kim Y, et al. "A 20 nucleotide upstream element is essential for the nopaline synthase (nos) promoter activity." Plant Mol. Biol. 24: 1–5–117, 1994.*
Mitsuhara I, et al. "Efficient promoter cassettes for enhanced expression of foreign genes in dicotyledonous and monocotyledonous plants." Plant Cell Physiol. 37: 49–59, 1996.*
Casacuberta et al., A gene coding for a basic pathogenesis–related (PR–like) protein from *Zea mays*. Molecular cloning and induction by a fungus (*Fusarium moniliforme*)in germinating maize seeds, Plant Molecular Biology, vol. 16(4):527–536 (1991).
Muradov et al., A cDNA clone for a pathogenesis–related protein 1 from barley, Plant Molecular Biology, vol. 23(2):439–442 (1993).
Raventos et al., A 20 bp cis–acting element is both necessary and sufficient to mediate elicitor response of a maize PRms gene, The Plant Journal, vol. 7(1):147–155 (1995).
Gillikin et al., Complete amino acid sequence of a polypeptide from *Zea mays* similar to the pathogenesis–related–1 family, Plant Physiol., vol. 96:1372–1375 (1991).
Varagona et al., (1990) "Implications for the Cis–Requirements for Ds Transposition Based on the Sequence of the wxB4 Ds Element," *Mol. Gen. Genet.* 220: 414–418.
Jutidamrongphan et al. (1989) "Sequence of a Near–Full–Length cDNA Clone for a mRNA of Barley Induced by Fungal Infection," *Nucleic Acids Res*. 17: 9478.
Lo et al. (1998) "Reduction of Light–Induced Anthocyanin Accumulation in Inoculated Sorghum Mesocotyls. Implications for a Compensatory Role in the Defense Response," *Plant Physiol*. 116: 979–989.
GenBank Report, Accession No. 1498731, Submitted Jul. 22, 1996.
GenBank Report, Accession No. 499074, Submitted Sep. 28, 1989.
GenBank Report, Accession No. 1408222, Submitted Jun. 13, 1996.
GenBank Report, Accession No. U82200, Submitted Dec. 13, 1996.
GneBank Report, Accession No. 100907, Submitted Feb. 1991.
GenBank Report, Accession No. 732807, Submitted Mar. 15, 1995.

\* cited by examiner

*Primary Examiner*—Amy J. Nelson
(74) *Attorney, Agent, or Firm*—Alston & Bird LLP

(57) ABSTRACT

The present invention provides compositions and methods for regulating expression of heterologous nucleotide sequences in a plant. Compositions are novel nucleotide sequences for inducible and constitutive promoters isolated from a family of maize genes encoding pathogenesis-related (PR-1) proteins. Methods for regulating expression of a heterologous nucleotide sequence in a plant in an inducible or constitutive manner are provided. The methods comprise transforming a plant cell to comprise a heterologous nucleotide sequence operably linked to one of the inducible or constitutive promoters of the present invention and regenerating a stably transformed plant from the transformed plant cell. Transformed plants and seeds are also provided.

17 Claims, 2 Drawing Sheets

SEQUENCE LISTING

```
<160> NUMBER OF SEQ ID NOS: 37

<210> SEQ ID NO 1
<211> LENGTH: 881
<212> TYPE: DNA
<213> ORGANISM: Zea mays

<400> SEQUENCE: 1
cgacggcccg ggctggtatc catgtcaatt ttgctgctac cgtcgggcga tcgcgtcctt      60
ggaattcttg cccctgtgga atttcttcta gctactaata acttgccgtc actgttgatt     120
gaccaaatgg gcagctactt tttgcagttt aattatactc tgtttccccc gatttgctac     180
ttactttgat cacaaatata tatttattta catttgttct aagtcagttt ttgataagct     240
aagaatatga aagtttttat tgtgcgcaaa cataagactt cccattatta gcttcatcgt     300
aaaaaataac atataagtac tcttttttta atatagcata aatttttatat cggtatactc     360
tttttattcaa tataatatag tataataatg acacatgtat aagtggccta ctattacaga    420
ctatatcgat cttctaaaag acttttaatt tgaaacctag ttggttaaat ttttcagagc     480
tgcttttgct taaataaact aaggatctat tttagtttgt gactaactat gccacatttt     540
gcctaaggtt agtcattcca attgaagaac tatctttagg cacaaaagtg taacaaaatg     600
tgacaaatta gcaggcgaac caaacagacc ctaaaagcaa ccaaaagagt tgttttctac     660
ccaagtactt caatggaagc agcttcttct ctagagcatc cttagatctg cttctctaga     720
gcatcctttg acatatcgat tgacaagcta gtcgccaagg tagccttttg ctaccactat     780
aaaaatacct gggcacacac gccacaactc acgcatccat ctaccacaca agaaacttca     840
tatttgttca tttgtctcca gcaatacgga ttccaaccat g                         881

<210> SEQ ID NO 2
<211> LENGTH: 1199
<212> TYPE: DNA
<213> ORGANISM: Zea mays
<220> FEATURE:
<221> NAME/KEY: unsure
<222> LOCATION: (195)
<223> OTHER INFORMATION: The nucleotide at this position may be a or g
      or t or c.
```

```
<400> SEQUENCE: 2
cgacggcccg ggctggttca aaaatagag agagttagct cttatgcaat tgacaagaaa      60
ytttatataag agcaaacttt aaagtcagct ttattatatg aatgtattta ttattattct    120
yataaatgaca tggtaaagag ttagaaccaa caataaactc tattattaaa cttgctctaa    180
yacctagaagc aaagntagtt gcagattcgc agttactaaa aaaaatgtgt catttaccttt   240
ytgtttatcgc agctcatgcc gtcactgatg accgcatcac acacatgcct ctccatccag    300
yacctgataga gtgtggtgcg taggcggcgt agctatcgta ttcgtagctc ctcgtgcccg    360
ycacgcttcga gaatgccact gaagtacggg gtcctgtagt actagtatat cttttggcag    420
ycatagacgac cgtcaccgtt atttgatatc gtgatggcga ttttttttaac accagatgac   480
yactctacaaa gatttttattg aatattcaat aaaaaatact cgacaaaaaa aattatcagt   540
yatacagttta tcaagacatc ttttgccgaa attcgtactt taccaaaagt ttttttagact  600
yttgccaagca gttgtatcta gtagtgatag taagacttac tttcaaacaa agaaaatatg    660
yaaagattttt aaatggttat ttttctactt aaaaattttc tacatgaatt tttggaacac    720
yaggattcaat catatcaatt ccatcgaaat tttctatgga ctgcatataa gttttggagg    780
yaaaaacacaa gaaatccaac ctcttggaaa cggtacgtac tatgactctt gtttctctat    840
ytcaaaatcct acatagctag catccaaagg ctaggtaaga aatttccgtg cgttctcaat    900
ytcatgtaggt tacaattttat agccaattct aattatatgt tttgtttatt gttctgtttt   960
tatattcctg tgttccaaag agggcctata atagaaacag gacctggaca tcgccatcgc    1020
catctgatga tctcgcaaat aataatgtag ggtatacaag agaggcagat ttgacagccg    1080
tcctactcca tttgctccta gtcccaaata ctagcaggcg gcaggcggcc aagaccggtg    1140
tccctcgacg acctgccgag tgccgaggca agacgcgagg aggctgtaat ggcgggcgc     1199

<210> SEQ ID NO 3
<211> LENGTH: 955
<212> TYPE: DNA
<213> ORGANISM: Zea mays

<400> SEQUENCE: 3
cgacggcccg ggctggtagt cttggttggg tcagatgtgg ccgataaaga tgaaggcaag      60
aacaatgtca ttggcgatcc tcgcacgcca agtcagttac aaggagtggt tacttgaaag    120
gctctgaaca agagaatgac taataagact caaggcccta gagggcaaac acgaccggat    180
acccgattac gatcacatgt cttgtgtacg caggacggtc cgggacctaa ggccgatcag    240
tctaagagtg accaaaagca acaacgacct cagaccttta gaccatgaca tctagaagaa    300
ggtatatgca agcaaaatac atctaaagca tctgactgac tcgttagtgc tagcccttct    360
tttgaacaac ttcttcctaa gtatatgaat aagaaggtcg tttcacacaa ttgatcgaca    420
aaacgatcaa tatcatccac aacgaggaag caatccatgc aagggcaaaa gccgaataaa    480
tcggcccagg aagtggtgca accaatgtcg cctactcatc cgctctagga atgtcgtgtt    540
actttccacc agtctactca tcgatgatgt tttatcctgc tgacatgtga aaaagtatga    600
cgatgaatcc gtatcacaca ggggcggacg cagagggagg caaagtgggt catagccacc    660
tcaatttttta tgatattta tatatcatga cgtgcagtct ctttgcaacc ccagccacat    720
taattaatag actccaccga cgagcgacga gtgatggtac cggccgccgg cccaggccaa    780
cccaagtgga aaaggccgac gactcccgga cgtctcatcc tcaccggacg ccaccaaccc    840
ccgcaatctc cagacgtacg agccgcctat ttaaagccct cagtctgcca ctctcatggc    900
```
aacgcaagca gaagctacaa tcctaaaacc atctgcttca gccttcagct agccc    955

<210> SEQ ID NO 4
<211> LENGTH: 1149
<212> TYPE: DNA
<213> ORGANISM: Zea mays

<400> SEQUENCE: 4
agtcgacggc ccgggctggt atctaagtat aatcgtattt ataaataatt tccgaggccc    60
cttttcctgt ctgatgaaga tcgctgaggc tgaacatgaa atgacagcag gtttcttat    120
tggccaagtc ccttgagaaa acctaatggt aaacaattag tcttctagaa ccctagcgaa    180
ccttgtacgc gttaagaaac ggattggtca agccagccga gatcatatga agtagatctt    240
ccgatagtaa ggaggtgctt ggtttgagga atcatttcat ccaaaatgta gtgatgcatc    300
atgggtccat tcctcaaatt tggtgggatg acctcatccc tcatattagt actaactaaa    360
taactataag gaatgaggtg atgatggatc aactcaatcc attccacaaa ccaaacaaaa    420
aagtgaggag tgagaagacg atggactaga tcattcctca aaccaaacag ctcataaagt    480
tcaaaactag agttgagaat aaaaactata gtatgcatga gcattaatct cggtctcaag    540
ttttatctgg ataagagtc catattagtc ctggttgtgg ttattcgaca aaatgtggat    600
cctttatcaa ttggaactaa ttaagggatt ttcacatgcc agttccgaag aaaagcgttc    660
tattcaccta ctatgtaggt gaggtaaaaa aaactactct gctaataata cttcattcct    720
tcttttttat ttttcatatt ttaatttgaa ataaaattaa ggatgaccaa tatttaagaa    780
tagatgtagt atatgagatg acgggttcaa gccttccaag ccaattttcc tgcttgtgtt    840
ctctagaatg ccgtgcccgt ccattttgta cctcctgctc ccagagtcta gtaaacgaaa    900
tccatgttta tccgaaaact ttcctgccga tcctatactg ttactcgcta atttattttt    960
aaactaaacc acgataaata aaaaaaacgg atgaagtata tgctatccaa taataccgtg   1020
gaaattcttg gctcccttgg aaggtcttga aggcgccacc attgaccgtg accatgccaa   1080
gtgcctacct tctgcaaatt atgctatata tcttgcttgg acttgcccct atatcgatt   1140
ataaatacc                                                           1149

<210> SEQ ID NO 5
<211> LENGTH: 255
<212> TYPE: DNA
<213> ORGANISM: Zea mays

<400> SEQUENCE: 5
cattctcgat cgatcttgat tagttattct tatatgagat gcatgggaga gagctaggtc    60
gtgttccggg tttttatagg cagtctctct ctctacatat ataatggtta ggtagctgag   120
tgagcgcagt gtgcgacttt gcgtgttatt ttttacacac aatgtgcgaa gcatgcatta   180
attaactcgg cacgcaagta ctatctctat catgcatgca ccagcccggg ccgtcgacca   240
cgcgtgccct atagt                                                    255

<210> SEQ ID NO 6
<211> LENGTH: 866
<212> TYPE: DNA
<213> ORGANISM: Zea mays
<220> FEATURE:
<221> NAME/KEY: CDS
<222> LOCATION: (111)..(581)

<400> SEQUENCE: 6

-continued

```
cccacgcgtc cgctaccaca caaaaacttc atatttgttc atttgtctcc agcaatataa      60
tggattactc gtctactagg gtcgtcgtgt gtttagctct ggcgttggcc atg gtc        116
                                                      Met Val
                                                        1 gcc gtg atg ccg tgc gcg gcc cag aac tcg ccg cag gac ttc gtg aac      164
Ala Val Met Pro Cys Ala Ala Gln Asn Ser Pro Gln Asp Phe Val Asn
      5                  10                  15 ccg cac aat gcg gcg cgc gcg gcc gtg ggc gtc ggc ccg gtg tcg tgg      212
Pro His Asn Ala Ala Arg Ala Ala Val Gly Val Gly Pro Val Ser Trp
 20                  25                  30 gat gag aac gtg gcc gcc ttc gcg cgg agc tac gcc gcg cag cgc cag      260
Asp Glu Asn Val Ala Ala Phe Ala Arg Ser Tyr Ala Ala Gln Arg Gln
 35                  40                  45                  50 ggc gac tgc aag ctg gtg cac tcc ggc ggc ggg ccc aac cac tac ggg      308
Gly Asp Cys Lys Leu Val His Ser Gly Gly Gly Pro Asn His Tyr Gly
                 55                  60                  65 gag aac atc ttc tgg ggc ggc ggc agc gcc tgg aag gcg tcg gac gcc      356
Glu Asn Ile Phe Trp Gly Gly Gly Ser Ala Trp Lys Ala Ser Asp Ala
             70                  75                  80 gtc ggc ttg tgg gtg ggg gag aag cag aac tac gat tac aac agc aac      404
Val Gly Leu Trp Val Gly Glu Lys Gln Asn Tyr Asp Tyr Asn Ser Asn
         85                  90                  95 agc tgc gcg gcg ggg aag gtg tgc ggc cac tac acg caa gtc gtc tgg      452
Ser Cys Ala Ala Gly Lys Val Cys Gly His Tyr Thr Gln Val Val Trp
100                 105                 110 cgc aaa tcc ccg cca tcg gct gcg ccc gcg tcg tct gca aca acg gcg      500
Arg Lys Ser Pro Pro Ser Ala Ala Pro Ala Ser Ser Ala Thr Thr Ala
115                 120                 125                 130 gtg gcg tct tca tca cct gca act aca acc cgc cgg gca act tcc gcg      548
Val Ala Ser Ser Ser Pro Ala Thr Thr Thr Arg Arg Ala Thr Ser Ala
                135                 140                 145 gac aga gac cct act agc tac cta gct agc tag ttccaatatc gattatacgc    601
Asp Arg Asp Pro Thr Ser Tyr Leu Ala Ser
                150                 155 gtacatatac tctacatgca tgttcagatc gatgatatat atacctcgcg tgcatgctac    661
cgattgaata aaccacaaac taagcttagg ccaccagttg attaggttta aagtgaacct    721
actcacccag gtttaagtga agtgtgcata catgtatgtg tatgttctgt gtggggtgtg    781
acagtttgtt tggtgtttca taaataaat aaatgaatga ataataagag tgttcatgag     841
caaaaaaaaa aaaaaaaaaa aaaaa                                          866
```

<210> SEQ ID NO 7
<211> LENGTH: 156
<212> TYPE: PRT
<213> ORGANISM: Zea mays

<400> SEQUENCE: 7

```
Met Val Ala Val Met Pro Cys Ala Ala Gln Asn Ser Pro Gln Asp Phe
  1               5                  10                  15

Val Asn Pro His Asn Ala Ala Arg Ala Ala Val Gly Val Gly Pro Val
             20                  25                  30

Ser Trp Asp Glu Asn Val Ala Ala Phe Ala Arg Ser Tyr Ala Ala Gln
         35                  40                  45

Arg Gln Gly Asp Cys Lys Leu Val His Ser Gly Gly Gly Pro Asn His
     50                  55                  60

Tyr Gly Glu Asn Ile Phe Trp Gly Gly Gly Ser Ala Trp Lys Ala Ser
 65                  70                  75                  80
```

-continued

```
Asp Ala Val Gly Leu Trp Val Gly Glu Lys Gln Asn Tyr Asp Tyr Asn
                 85                  90                  95

Ser Asn Ser Cys Ala Ala Gly Lys Val Cys Gly His Tyr Thr Gln Val
            100                 105                 110

Val Trp Arg Lys Ser Pro Pro Ser Ala Ala Pro Ala Ser Ser Ala Thr
        115                 120                 125

Thr Ala Val Ala Ser Ser Pro Ala Thr Thr Arg Arg Ala Thr
    130                 135                 140

Ser Ala Asp Arg Asp Pro Thr Ser Tyr Leu Ala Ser
145                 150                 155

<210> SEQ ID NO 8
<211> LENGTH: 973
<212> TYPE: DNA
<213> ORGANISM: Zea mays
<220> FEATURE:
<221> NAME/KEY: CDS
<222> LOCATION: (102)..(797)

<400> SEQUENCE: 8
tcgaccacgc gtccggtccc aatactagca ggcggcagcg gccaagaccg gtgtccctcg      60
acgacctgcc gagtgccgag gcaagacgcg aggaggctgt a atg gcg ggc gcc gag    116
                                             Met Ala Gly Ala Glu
                                               1               5 gtg gga gaa gac aag tac cgc tcc ttc atc cac ggc gag ggc gag agg      164
Val Gly Glu Asp Lys Tyr Arg Ser Phe Ile His Gly Glu Gly Glu Arg
             10                  15                  20 gac acc gtg tgg agg tac ggc gcc ccg ccc aac tac gac gtg gtc aac      212
Asp Thr Val Trp Arg Tyr Gly Ala Pro Pro Asn Tyr Asp Val Val Asn
         25                  30                  35 aag ctc ttc gag gaa gag agg act cag gtg tgg ccc gag ggc tcg ctg      260
Lys Leu Phe Glu Glu Glu Arg Thr Gln Val Trp Pro Glu Gly Ser Leu
     40                  45                  50 gag gag aag gtg cag cgg ctg ctc aag agc tgg gag atg gag ttg gtg      308
Glu Glu Lys Val Gln Arg Leu Leu Lys Ser Trp Glu Met Glu Leu Val
 55                  60                  65 cac aag gcg cgg ccc gag gac cag aag acc gtc aac tcg gag aaa tac      356
His Lys Ala Arg Pro Glu Asp Gln Lys Thr Val Asn Ser Glu Lys Tyr
 70                  75                  80                  85 tct gcc agc acc aac ggg atg agc gct ctg acc cgg gcc gag gtg atg      404
Ser Ala Ser Thr Asn Gly Met Ser Ala Leu Thr Arg Ala Glu Val Met
                 90                  95                 100 gcc atc ggc ggc tac aac aac ttc ctg cgc acc aag ctg ccc ccg gag      452
Ala Ile Gly Gly Tyr Asn Asn Phe Leu Arg Thr Lys Leu Pro Pro Glu
            105                 110                 115 cac cgc atc tac gac ccg gac agc gag acc gtg gag tcc gcc atg gcc      500
His Arg Ile Tyr Asp Pro Asp Ser Glu Thr Val Glu Ser Ala Met Ala
        120                 125                 130 acc ttc acc acg gcc ttc ccg cgg ggc ttc gcc atc gag gtg ctc gac      548
Thr Phe Thr Thr Ala Phe Pro Arg Gly Phe Ala Ile Glu Val Leu Asp
    135                 140                 145 gtc tac agc ggc ccg ccc agg atc gcc ttc aag ttc cgc cac tgg ggc      596
Val Tyr Ser Gly Pro Pro Arg Ile Ala Phe Lys Phe Arg His Trp Gly
150                 155                 160                 165 tac atg gag ggg ccc ttc aag ggc cac ccg ccg cac ggc cag cgg gtc      644
Tyr Met Glu Gly Pro Phe Lys Gly His Pro Pro His Gly Gln Arg Val
                170                 175                 180 gag ctc ttc ggc gtc tgc atc ttc cat gtt gac gaa gac atg aag gtg      692
Glu Leu Phe Gly Val Cys Ile Phe His Val Asp Glu Asp Met Lys Val
```

-continued

```
                        185                 190                 195
gac aag tca gag tac ttc tac gag cgc ggc aac ttc ctc gcc ggc ttc      740
Asp Lys Ser Glu Tyr Phe Tyr Glu Arg Gly Asn Phe Leu Ala Gly Phe
        200                 205                 210 ttg agt gcc cct gcc cct gat ggc tca ggc ggt tgc ccc gtg atg cgc      788
Leu Ser Ala Pro Ala Pro Asp Gly Ser Gly Gly Cys Pro Val Met Arg
    215                 220                 225 ggg aac tga atgggcctgc aatgggacat tggaagacta ggcattggaa              837
Gly Asn
230 cattgggatt attagcatta gcgatcccga atccgctttt attacggttt aataattcca    897 tcatgtaaca tgacacttgc atttgtgttt gaataaacat ttcagttgct tccaaaaaaa    957 aaaaaaaaaa aaaaaa                                                    973

<210> SEQ ID NO 9
<211> LENGTH: 231
<212> TYPE: PRT
<213> ORGANISM: Zea mays

<400> SEQUENCE: 9

Met Ala Gly Ala Glu Val Gly Glu Asp Lys Tyr Arg Ser Phe Ile His
 1               5                  10                  15

Gly Glu Gly Glu Arg Asp Thr Val Trp Arg Tyr Gly Ala Pro Pro Asn
                20                  25                  30

Tyr Asp Val Val Asn Lys Leu Phe Glu Glu Arg Thr Gln Val Trp
            35                  40                  45

Pro Glu Gly Ser Leu Glu Glu Lys Val Gln Arg Leu Leu Lys Ser Trp
        50                  55                  60

Glu Met Glu Leu Val His Lys Ala Arg Pro Glu Asp Gln Lys Thr Val
 65                  70                  75                  80

Asn Ser Glu Lys Tyr Ser Ala Ser Thr Asn Gly Met Ser Ala Leu Thr
                85                  90                  95

Arg Ala Glu Val Met Ala Ile Gly Gly Tyr Asn Asn Phe Leu Arg Thr
                100                 105                 110

Lys Leu Pro Pro Glu His Arg Ile Tyr Asp Pro Asp Ser Glu Thr Val
            115                 120                 125

Glu Ser Ala Met Ala Thr Phe Thr Thr Ala Phe Pro Arg Gly Phe Ala
        130                 135                 140

Ile Glu Val Leu Asp Val Tyr Ser Gly Pro Pro Arg Ile Ala Phe Lys
145                 150                 155                 160

Phe Arg His Trp Gly Tyr Met Glu Gly Pro Phe Lys Gly His Pro Pro
                165                 170                 175

His Gly Gln Arg Val Glu Leu Phe Gly Val Cys Ile Phe His Val Asp
            180                 185                 190

Glu Asp Met Lys Val Asp Lys Ser Glu Tyr Phe Tyr Glu Arg Gly Asn
        195                 200                 205

Phe Leu Ala Gly Phe Leu Ser Ala Pro Ala Pro Asp Gly Ser Gly Gly
    210                 215                 220

Cys Pro Val Met Arg Gly Asn
225                 230

<210> SEQ ID NO 10
<211> LENGTH: 887
<212> TYPE: DNA
<213> ORGANISM: Zea mays
<220> FEATURE:
```

<221> NAME/KEY: CDS
<222> LOCATION: (93)..(575)

<400> SEQUENCE: 10

```
cccacgcgtc cggaagctac aatcctaaaa ccatctgctt cagccttcag ctagccccaa        60
gtttagtcgg ccgatcgatc actgaagtag ta atg gcc tcc gcc aac agc tgg        113
                                   Met Ala Ser Ala Asn Ser Trp
                                    1               5 acc ctc gag atc gcg tcg ccg gtg gct ccg cag cgc ctg ttc cgc gcc        161
Thr Leu Glu Ile Ala Ser Pro Val Ala Pro Gln Arg Leu Phe Arg Ala
         10                  15                  20 gcc gtg atg gac tgg cac acc ctg gcg ccc aag gtc gcc tcc cac gtc        209
Ala Val Met Asp Trp His Thr Leu Ala Pro Lys Val Ala Ser His Val
 25                  30                  35 gtc gcc agc gcg cag ccc gtg gag ggc gac ggc ggt gtt ggc agc gtc        257
Val Ala Ser Ala Gln Pro Val Glu Gly Asp Gly Gly Val Gly Ser Val
 40                  45                  50                  55 agg cag ttc aac ttc acc tca gtc atg ccg ttc agc ttc atg aag gag        305
Arg Gln Phe Asn Phe Thr Ser Val Met Pro Phe Ser Phe Met Lys Glu
                 60                  65                  70 agg ctc gag ttc ctg gac gcg gac aag tgc gag tgc aag aac acg ctc        353
Arg Leu Glu Phe Leu Asp Ala Asp Lys Cys Glu Cys Lys Asn Thr Leu
             75                  80                  85 atc gag ggc ggc ggc atc ggc gtc gcc atc gaa acg gcg acg tcg cac        401
Ile Glu Gly Gly Gly Ile Gly Val Ala Ile Glu Thr Ala Thr Ser His
         90                  95                 100 atc aag gtg gag ccc gcg gcc ggc ggc ggg agc gtg gtg aag gtc gaa        449
Ile Lys Val Glu Pro Ala Ala Gly Gly Gly Ser Val Val Lys Val Glu
     105                 110                 115 tcc act tac aag ctg ctg ccg ggc gtg gag gtg aag gac gag atc gcc        497
Ser Thr Tyr Lys Leu Leu Pro Gly Val Glu Val Lys Asp Glu Ile Ala
120                 125                 130                 135 aag gcc aag gag tcc gtc acc gcc atc ttc aag ggt gcc gag gcc tac        545
Lys Ala Lys Glu Ser Val Thr Ala Ile Phe Lys Gly Ala Glu Ala Tyr
                 140                 145                 150 ctc gtc gcc aac ccc gac gcc tac aac taa accattggac tgggatgagc        595
Leu Val Ala Asn Pro Asp Ala Tyr Asn
             155                 160 ttcatttccc ttccgtcttg tttggatata caagggtatt gtgtacggag attgggtttt       655
ctttccccct cttttttgtt ttcatacaaa ataaaataaa gctgctctaa agcagcgtgc       715 ggttttttgga ctcgagatgg tatgattata tatatgtacg tgctgtcctt gtgttgtata     775
ccgtcatggt tttctgtgtg ggaagaaaaa gggcattctg ttttagaatc ctatgtaggt       835
ttgactgaat aaggaatttt acttgctcaa aaaaaaaaa aaaaaaaaaa aa               887
```

<210> SEQ ID NO 11
<211> LENGTH: 160
<212> TYPE: PRT
<213> ORGANISM: Zea mays

<400> SEQUENCE: 11

```
Met Ala Ser Ala Asn Ser Trp Thr Leu Glu Ile Ala Ser Pro Val Ala
 1               5                  10                  15

Pro Gln Arg Leu Phe Arg Ala Ala Val Met Asp Trp His Thr Leu Ala
             20                  25                  30

Pro Lys Val Ala Ser His Val Val Ala Ser Ala Gln Pro Val Glu Gly
         35                  40                  45

Asp Gly Gly Val Gly Ser Val Arg Gln Phe Asn Phe Thr Ser Val Met
```

```
            50                   55                   60
Pro Phe Ser Phe Met Lys Glu Arg Leu Glu Phe Leu Asp Ala Asp Lys
 65                   70                   75                   80

Cys Glu Cys Lys Asn Thr Leu Ile Glu Gly Gly Gly Ile Gly Val Ala
                 85                   90                   95

Ile Glu Thr Ala Thr Ser His Ile Lys Val Glu Pro Ala Ala Gly Gly
            100                  105                  110

Gly Ser Val Val Lys Val Glu Ser Thr Tyr Lys Leu Leu Pro Gly Val
            115                  120                  125

Glu Val Lys Asp Glu Ile Ala Lys Ala Lys Glu Ser Val Thr Ala Ile
            130                  135                  140

Phe Lys Gly Ala Glu Ala Tyr Leu Val Ala Asn Pro Asp Ala Tyr Asn
145                  150                  155                  160

<210> SEQ ID NO 12
<211> LENGTH: 749
<212> TYPE: DNA
<213> ORGANISM: Zea mays
<220> FEATURE:
<221> NAME/KEY: CDS
<222> LOCATION: (92)..(583)

<400> SEQUENCE: 12
cccacgcgtc cgcccacgcg tccgccgatc acacattgga cttgcactgg tgcttgctca      60
taattactag ttcatcagca aacaacaaac a atg gca ccg agg cta gcg tgc        112
                                   Met Ala Pro Arg Leu Ala Cys
                                    1               5 ctc cta gct ctg gcc atg gca gcc atc gtc gtg gcg ccg tgc acg gcc       160
Leu Leu Ala Leu Ala Met Ala Ala Ile Val Val Ala Pro Cys Thr Ala
         10                  15                  20 cag aac tcg ccg cag gac tac gtg gac ccg cac aac gcg gcg cgc gcc       208
Gln Asn Ser Pro Gln Asp Tyr Val Asp Pro His Asn Ala Ala Arg Ala
 25                  30                  35 gac gtg ggc gtc ggg ccg gtg tcc tgg gac gac acc gtc gcc gcg tac       256
Asp Val Gly Val Gly Pro Val Ser Trp Asp Asp Thr Val Ala Ala Tyr
 40                  45                  50                  55 gcg cag agc tac gcg gcg cag cgc cag ggc gac tgc cag ctg atc cac       304
Ala Gln Ser Tyr Ala Ala Gln Arg Gln Gly Asp Cys Gln Leu Ile His
                 60                  65                  70 tcc ggc ggg ccc tac ggc gag aac ctc ttc tgg ggc tcc gcc ggc gcc       352
Ser Gly Gly Pro Tyr Gly Glu Asn Leu Phe Trp Gly Ser Ala Gly Ala
             75                  80                  85 gac tgg tcg gcg tcc gac gcc gtg ggc tcc tgg gtg tcc gag aag cag       400
Asp Trp Ser Ala Ser Asp Ala Val Gly Ser Trp Val Ser Glu Lys Gln
         90                  95                 100 tac tac gac cac gac acc aac agc tgc gcg gag ggg cag gtg tgc ggc       448
Tyr Tyr Asp His Asp Thr Asn Ser Cys Ala Glu Gly Gln Val Cys Gly
    105                 110                 115 cac tac acg cag gtg gtg tgg cgc gac tcc acc gcc atc ggc tgt gcc       496
His Tyr Thr Gln Val Val Trp Arg Asp Ser Thr Ala Ile Gly Cys Ala
120                 125                 130                 135 cgc gtc gtc tgc gac aac aac gcc ggc gtc ttc atc atc tgc agc tac       544
Arg Val Val Cys Asp Asn Asn Ala Gly Val Phe Ile Ile Cys Ser Tyr
                140                 145                 150 aac ccg ccg ggc aac gtc gtc ggc gag agc ccc tac tag actgtcatgc        593
Asn Pro Pro Gly Asn Val Val Gly Glu Ser Pro Tyr
            155                 160 atactacaat tatatattta tatacgctta atattaattt cagcatgcat gcatattata     653
```

-continued

```
aatagtgttg tcaactctgt atatcattat attacgatga ttatattgtt gatgaacata    713
ataagtcaat aaaaccatgc aggcgatttg tgagcc    749
```

<210> SEQ ID NO 13
<211> LENGTH: 163
<212> TYPE: PRT
<213> ORGANISM: Zea mays

<400> SEQUENCE: 13

```
Met Ala Pro Arg Leu Ala Cys Leu Leu Ala Leu Ala Met Ala Ala Ile
 1               5                  10                  15

Val Val Ala Pro Cys Thr Ala Gln Asn Ser Pro Gln Asp Tyr Val Asp
             20                  25                  30

Pro His Asn Ala Ala Arg Ala Asp Val Gly Val Gly Pro Val Ser Trp
         35                  40                  45

Asp Asp Thr Val Ala Ala Tyr Ala Gln Ser Tyr Ala Ala Gln Arg Gln
     50                  55                  60

Gly Asp Cys Gln Leu Ile His Ser Gly Gly Pro Tyr Gly Glu Asn Leu
 65                  70                  75                  80

Phe Trp Gly Ser Ala Gly Ala Asp Trp Ser Ala Ser Asp Ala Val Gly
                 85                  90                  95

Ser Trp Val Ser Glu Lys Gln Tyr Tyr Asp His Asp Thr Asn Ser Cys
            100                 105                 110

Ala Glu Gly Gln Val Cys Gly His Tyr Thr Gln Val Val Trp Arg Asp
        115                 120                 125

Ser Thr Ala Ile Gly Cys Ala Arg Val Val Cys Asp Asn Asn Ala Gly
    130                 135                 140

Val Phe Ile Ile Cys Ser Tyr Asn Pro Pro Gly Asn Val Val Gly Glu
145                 150                 155                 160

Ser Pro Tyr
```

<210> SEQ ID NO 14
<211> LENGTH: 806
<212> TYPE: DNA
<213> ORGANISM: Zea mays
<220> FEATURE:
<221> NAME/KEY: CDS
<222> LOCATION: (42)..(686)
<220> FEATURE:
<221> NAME/KEY: unsure
<222> LOCATION: (775)
<223> OTHER INFORMATION: The nucleotide at this position may be a or g
      or t or c.

<400> SEQUENCE: 14

```
cgacccacgc gtccggaata actaatcaag atcgatcgag a atg gcg ttt ccg aag    56
                                             Met Ala Phe Pro Lys
                                              1               5 cct act agt cgt cta gcc gcg cta gct gcc ctc gct gcg gcc atg gcg    104
Pro Thr Ser Arg Leu Ala Ala Leu Ala Ala Leu Ala Ala Ala Met Ala
                10                  15                  20 gcg gcg atg atg gcc gcg acc gcc tcg gcg cag aac acg ccg cag gac    152
Ala Ala Met Met Ala Ala Thr Ala Ser Ala Gln Asn Thr Pro Gln Asp
             25                  30                  35 ttc gtg aat ctg cac aac cgc gcg cgc gcg gcg gac ggc gtg ggc ccg    200
Phe Val Asn Leu His Asn Arg Ala Arg Ala Ala Asp Gly Val Gly Pro
         40                  45                  50 gtg gcg tgg gac gcc agg gtg gcc agg tac gcg cag gac tac gcg gcg    248
Val Ala Trp Asp Ala Arg Val Ala Arg Tyr Ala Gln Asp Tyr Ala Ala
```

|  |  |  |  |  |  |  |  |  |  |  |  |  |  |  |  |
|---|---|---|---|---|---|---|---|---|---|---|---|---|---|---|---|
| | 55 | | | | 60 | | | | | 65 | | | | | |

```
aag cgc gcc ggg gac tgc cgg ctg gtg cac tcg ggg ggg ccg ttc ggc       296
Lys Arg Ala Gly Asp Cys Arg Leu Val His Ser Gly Gly Pro Phe Gly
 70                  75                  80                  85 gag agc atc ttc tgg ggc tcg gcg ggg cgg gcg tgg agc gcc gcc gac       344
Glu Ser Ile Phe Trp Gly Ser Ala Gly Arg Ala Trp Ser Ala Ala Asp
                 90                  95                 100 gcg ctg cgg tcg tgg gtg gac gag aag agg aac tac cac ctg agc agc       392
Ala Leu Arg Ser Trp Val Asp Glu Lys Arg Asn Tyr His Leu Ser Ser
            105                 110                 115 aac acc tgc gac ccc ggc aag gtg tgc ggc cac tac acg cag gtg gtg       440
Asn Thr Cys Asp Pro Gly Lys Val Cys Gly His Tyr Thr Gln Val Val
        120                 125                 130 tgg cgc agg tgt cca ccc gca tcg gct gcg cgc gcg tcg tct gcg ccg       488
Trp Arg Arg Cys Pro Pro Ala Ser Ala Ala Arg Ala Ser Ser Ala Pro
    135                 140                 145 aca acc gcg gcg tct tca tcg tct gca gct acg acc ccc cgg gca acg       536
Thr Thr Ala Ala Ser Ser Ser Ala Ala Thr Thr Pro Arg Ala Thr
150                 155                 160                 165 tca acg gcc agc gcc cgt tcc tca ctc tcg acg cgg ctg cca agt aga       584
Ser Thr Ala Ser Ala Arg Ser Ser Leu Ser Thr Arg Leu Pro Ser Arg
                170                 175                 180 ggc aga gag ccc ggc tgc atg cag tgt gcg tac gca cgc atc tgc gtg       632
Gly Arg Glu Pro Gly Cys Met Gln Cys Ala Tyr Ala Arg Ile Cys Val
            185                 190                 195 tgc atg gcg tgg cta ctc gat cga tca cgt act gcg tgt gcg cgc gca       680
Cys Met Ala Trp Leu Leu Asp Arg Ser Arg Thr Ala Cys Ala Arg Ala
        200                 205                 210 cca taa taagtattgt gtgtacgtat atatctgcat ctgcagtgtt tgtgtcatat       736
Pro
215 ataaataat cgtctgcgtg cgctatataa tatctatana acttcaataa ttttacataa      796
aaaaaaaaaa                                                            806

<210> SEQ ID NO 15
<211> LENGTH: 214
<212> TYPE: PRT
<213> ORGANISM: Zea mays

<400> SEQUENCE: 15

Met Ala Phe Pro Lys Pro Thr Ser Arg Leu Ala Ala Leu Ala Ala Leu
  1               5                  10                  15

Ala Ala Ala Met Ala Ala Ala Met Met Ala Ala Thr Ala Ser Ala Gln
             20                  25                  30

Asn Thr Pro Gln Asp Phe Val Asn Leu His Asn Arg Ala Arg Ala Ala
         35                  40                  45

Asp Gly Val Gly Pro Val Ala Trp Asp Ala Arg Val Ala Arg Tyr Ala
     50                  55                  60

Gln Asp Tyr Ala Ala Lys Arg Ala Gly Asp Cys Arg Leu Val His Ser
 65                  70                  75                  80

Gly Gly Pro Phe Gly Glu Ser Ile Phe Trp Gly Ser Ala Gly Arg Ala
                 85                  90                  95

Trp Ser Ala Ala Asp Ala Leu Arg Ser Trp Val Asp Glu Lys Arg Asn
            100                 105                 110

Tyr His Leu Ser Ser Asn Thr Cys Asp Pro Gly Lys Val Cys Gly His
        115                 120                 125

Tyr Thr Gln Val Val Trp Arg Arg Cys Pro Pro Ala Ser Ala Ala Arg
```

```
              130                 135                 140
Ala Ser Ser Ala Pro Thr Thr Ala Ala Ser Ser Ser Ser Ala Thr
145                 150                 155                 160

Thr Pro Arg Ala Thr Ser Thr Ala Ser Ala Arg Ser Ser Leu Ser Thr
                165                 170                 175

Arg Leu Pro Ser Arg Gly Arg Glu Pro Gly Cys Met Gln Cys Ala Tyr
            180                 185                 190

Ala Arg Ile Cys Val Cys Met Ala Trp Leu Leu Asp Arg Ser Arg Thr
        195                 200                 205

Ala Cys Ala Arg Ala Pro
    210

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 16
gtaatacgac tcactatagg gc                                              22

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 17
agctaaacac acgacgaccc tagtagacga                                      30

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 18
ctcccacctc ggcgcccgcc attacag                                         27

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 19
gccagtccat cacggcggcg cggaacag                                        28

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 20
```
cacgctagcc tcggtgccat tgtttgttgt                                        30

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 21
ggctagacga ctagtaggct tcggaaa                                           27

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: PCR primer

<400> SEQUENCE: 22
actatagggc acgcgtggt                                                    19

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 23
gcacggcatc acggcgacca tggccaa                                           27

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 24
gcgcccgcca ttacagcctc ctcgcgtctt                                        30

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 25
gggctagctg aaggctgaag cagatgg                                           27

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 26
gacgatggct gccatggcca cagctaggag                                        30

```
<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 27
ccatggccgc agcgagggca gctagcg                                              27

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 28
gctaccacac aaaaacttca tatttg                                               26

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 29
gcatcacggc gaccatggcc aac                                                  23

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 30
aggcggcagc ggccaagacc ggtgt                                                25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 31
ggtgtccctc tcgccctcgc cgtgg                                                25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 32
cccacgcgtc cggaagctac aatcc                                                25

<210> SEQ ID NO 33
<211> LENGTH: 23
<212> TYPE: DNA
<213> ORGANISM: Artificial Sequence
```

-continued

```
<220> FEATURE:
<223> OTHER INFORMATION: Description of Artificial Sequence: Maize
      gene-specific PCR primer

<400> SEQUENCE: 33
gccaccggcg acgcgatctc gag                                             23

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 34
cattggactt gcactggtgc ttgc                                            24

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 35
gcgccacgac gatggctgcc atg                                             23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 36
gaataactaa tcaagatcga tcg                                             23

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Maize
      gene-specific PCR primer

<400> SEQUENCE: 37
cgccgaggcg gtcgcggcca tc                                              22
```

MAIZE PR-1 GENE PROMOTERS

CROSS-REFERENCE TO RELATED APPLICATIONS

This application claims the benefit of U.S. Provisional Application Ser. No. 60/076,100, filed Feb. 26, 1998, and U.S. Provisional Application Ser. No. 60/079,648, filed Mar. 27, 1998, the disclosures of which are herein incorporated by reference.

FIELD OF THE INVENTION

The present invention relates to the field of plant molecular biology, more particularly to regulation of gene expression and enhancing disease resistance in plants.

BACKGROUND OF THE INVENTION

Disease in plants is caused by biotic and abiotic causes. Biotic causes include fungi, viruses, bacteria, and nematodes. Of these, fungi are the most frequent causative agent of disease on plants. Abiotic causes of disease in plants include extremes of temperature, water, oxygen, soil pH, plus nutrient-element deficiencies and imbalances, excess heavy metals, and air pollution.

A host of cellular processes enables plants to defend themselves from disease caused by pathogenic agents. These processes apparently form an integrated set of resistance mechanisms that is activated by initial infection and then limits further spread of the invading pathogenic microorganism.

Subsequent to recognition of a potentially pathogenic microbe, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often neighboring cells, rapidly collapse and dry in a necrotic fleck. Other responses include the deposition of callose, the physical thickening of cell walls by lignification, and the synthesis of various antibiotic small molecules and proteins, among which are the pathogenesis-related (PR) proteins. Genetic factors in both the host and the pathogen determine the specificity of these local responses, which can be very effective in limiting the spread of infection.

Pathogenesis-related proteins, which have been described in a number of plants (see Bowles (1990) *Ann. Rev. Biochem.* 59:873–907 for review), include the PR-1 proteins. Although their biochemical functions remain unknown, expression of PR-1 proteins is generally induced by pathogens and many abiotic treatments associated with the elicitation of the defense response, more particularly a hypersensitive response (see WO 89/02437 for a review). In tobacco, PR-1 protein expression is induced by viral infection and salicylic acid (SA) treatment (van Loon et al. (1987) *Plant Mol. Biol.* 9:593; Ward et al. (1991) *Plant Cell* 3:1085). Barley plants resistant to powdery mildew caused by *Erysiphe graminis* accumulate PRb-1 (a basic PR-1) mRNA 12 hours after inoculation with that pathogen, while susceptible plants do not, indicating these proteins serve as antipathogenic agents that contribute to disease resistance. Ethylene, jasmonic acid (JA), and SA also induce the accumulation of PRb-1 in the resistant cultivars, but not in related susceptible lines (Muradov et al. (1993) *Plant Mol. Biol.* 23:439). Salicylic acid induces PR-1 protein accumulation in maize leaves. Ultraviolet light and *C. carbonum* (tox-) inoculations induce protein accumulation in Pr (hml) leaves (in Crane et al. (1996), *Biology of Plant-Microbe Interactions* (International Society for Molecular Plant-Microbe Interactions), pp. 223–226). These observations make maize PR-1 genes and their promoters ideal candidates for use in the development of transgenic plants, particularly transgenic plants having enhanced disease resistance.

Thus, isolation and characterization of PR-1 genes and their corresponding promoters, which can serve as regulatory regions for expression of their native gene or other heterologous nucleotide sequences of interest, are needed for genetic manipulation of plants to exhibit specific phenotypic traits, particularly enhanced disease resistance, either in response to a given stimulus or in a constitutive manner.

SUMMARY OF THE INVENTION

Compositions and methods for regulating gene expression in a plant are provided. Compositions are novel nucleotide sequences for inducible and constitutive plant promoters, more particularly promoters isolated from a family of maize genes encoding pathogenesis-related PR-1 proteins. Methods for regulating expression of a nucleotide sequence of interest in a plant using the promoter sequences disclosed herein are provided. The methods comprise transforming a plant cell with a nucleotide sequence of interest that is operably linked to one of the plant promoters of the present invention and regenerating a stably transformed plant from the transformed plant cell. Where the promoter is an inducible promoter of the invention, exposure of the transformed plant, or a particular tissue of the plant, to a stimulus activates, within the exposed tissues of the plant, expression of the nucleotide sequence operably linked to the particular inducible promoter disclosed herein.

Compositions of the invention also include the nucleotide sequences for novel maize PR-1 genes and the predicted amino acid sequences for the pathogenesis-related proteins encoded thereby. These nucleotide sequences are useful in the genetic manipulation of any plant when operably linked to a promoter that drives expression of a coding sequence in a plant cell, more particularly the PR-1 inducible and constitutive promoters disclosed herein. In this manner, transformed plants and progeny having increased resistance to pathogens and their related diseases may be obtained.

DETAILED DESCRIPTION OF THE INVENTION

Figure 1:
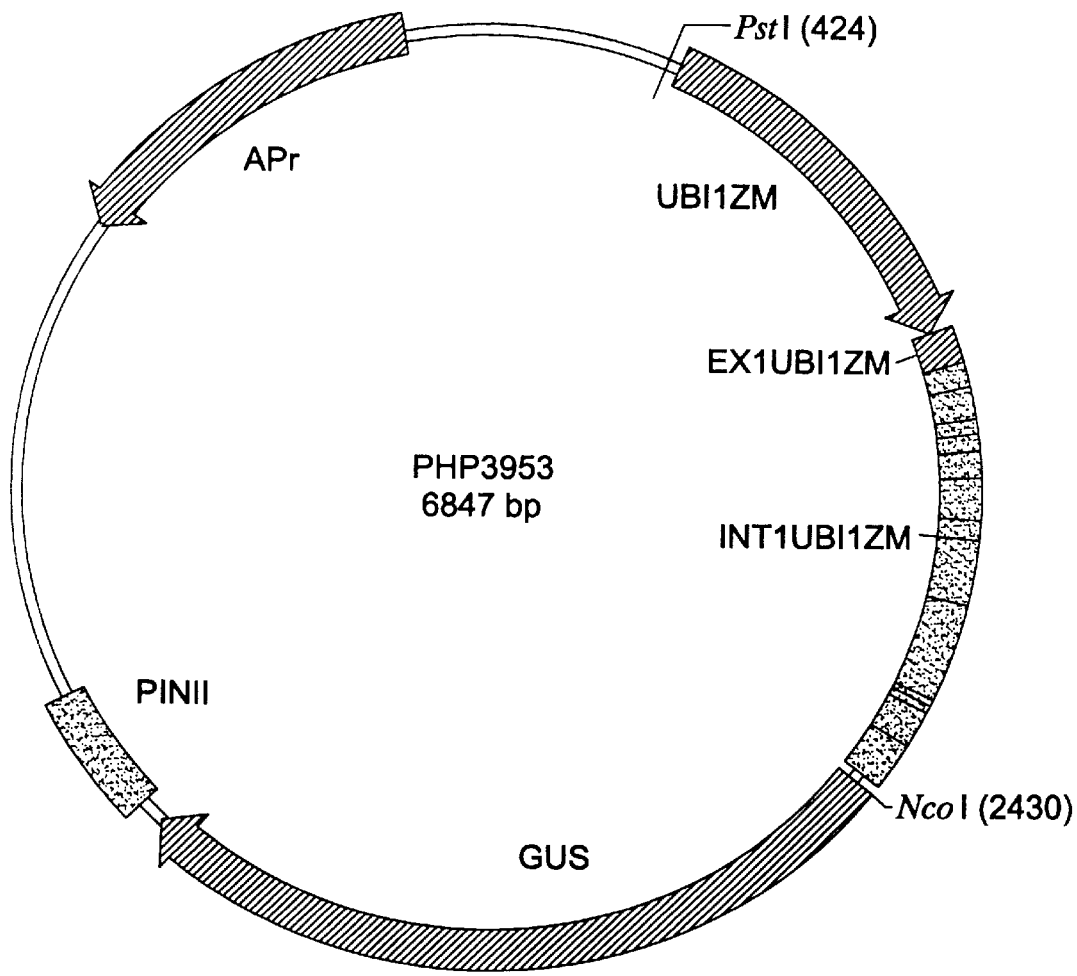
FIG. 1 shows the plasmid vector PHP3953 comprising the GUS gene operably linked to the ubiquitin promoter. Promoter fragments of the present invention were recloned into this plasmid in place of the ubiquitin promoter, and the resulting plasmid DNA was available for use in transformation studies to test for promoter activity.

Compositions of the present invention are nucleic acid molecules comprising novel nucleotide sequences for plant promoters for five maize genes, hereinafter designated as PR-1#52, PR-1#70, PR-1#81, PR-1#83, and PR-1#93, nucleotide sequences and respective predicted amino acid sequences for the pathogenesis-related class I (PR-1) proteins encoded by four of these maize genes. Nucleotide sequences for the promoters of these PR-1 genes are set forth in SEQ ID NOs: 1–5, respectively. Nucleotide sequences for the maize PR-1 genes PR-1#52, PR-1#70, PR-1#81, PR-1#83, and PR-1#93 are set forth in SEQ ID NOs: 6, 8, 10, 12, and 14, respectively. Amino acid sequences for the PR-1 proteins encoded by these genes are set forth in SEQ ID NOs: 7, 9, 11, 13, and 15, respectively. Four of these genes, Pr-1#52, PR-1#70, PR-1#81, and PR-1#93 are novel. PR-1#83 is homologous to a known maize PR-1 gene, the cDNA sequence of which is published as GenBank Accession No. U82200. The PR-1 promoters of the invention were isolated from the 5' untranslated region flanking their respective transcription initiation sites. Methods for isolation of promoter regions are well known in the art. The specific method used to obtain the promoters of the present invention is described in Example 1 below.

In particular, the present invention provides for isolated nucleic acid molecules comprising nucleotide sequences for plant promoters shown in SEQ ID NOs: 1–5, nucleotide sequences encoding the amino acid sequences shown in SEQ ID NOs: 7, 9, 11, and 15, or the nucleotide sequences encoding the DNA sequences deposited in a bacterial host as ATCC Accession Nos. 207130 (PR-1#52 promoter), 207138 (PR-1#70 promoter) 207139 (PR-1#81 promoter), 207131 (PR-1#83 promoter), 207132 (PR-1#93 promoter), 20207134 (PR-1#52 gene), 207136 (PR-1#70 gene), 207135 (PR-1#81 gene) 207133 (PR-1#83 gene) and 207137 (PR-1#93 gene). Further provided are polypeptides having an amino acid sequence encoded by a nucleic acid molecule described herein, for example those set forth in SEQ ID NOs: 6, 8, 10, and 14, those deposited as ATCC Accession Nos. 207134, 207136, 207135 and 207137, and fragments and variants thereof.

Plasmids containing the PR-1 promoter and gene nucleotide sequences of the invention were deposited on Feb. 26, 1999 with American Type Culture Collection (ATCC), Manassas, Va., and assigned Accession Nos. 207130, 207138, 207139, 207131, 207132, 207134, 207136, 207135, 207133, and 207137. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

Thus, the invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid molecule is free of sequences (preferably protein encoding sequences) that naturally flank the nucleic acid molecule (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid molecule is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably, culture medium represents less than about 30%, 20%, 10%, or 5% (by dry weight) of chemical precursors or non-protein-of-interest chemicals.

The compositions of the invention include isolated nucleic acid molecules comprising the promoter nucleotide sequences set forth in SEQ ID NOS: 1–5. By "promoter" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Thus, for example, the promoter regions disclosed herein may further comprise upstream regulatory elements that confer tissue-specific expression of any heterologous nucleotide sequence operably linked to one of the disclosed promoter sequences. See particularly Australian Patent No. AU-A-77751/94 and U.S. Pat. Nos. 5,466,785 and 5,635,618. Depending upon the promoter sequence utilized, the pattern of expression will be inducible, for example, with the promoter sequences disclosed in SEQ ID NOs: 1–4, or constitutive, for example, with the promoter sequence disclosed in SEQ ID NO: 5.

The maize inducible and constitutive promoter sequences of the present invention, when assembled within a DNA construct such that the promoter is operably linked to a heterologous nucleotide sequence of interest, enable expression of the heterologous nucleotide sequence in the cells of a plant stably transformed with this DNA construct. By "heterologous nucleotide sequence" is intended a sequence that is not naturally occurring with the promoter sequence. While this nucleotide sequence is heterologous to the promoter sequence, it may be homologous, or native, or heterologous, or foreign, to the plant host. Choice of the promoter sequence will determine when and where within the organism the heterologous nucleotide sequence is expressed. Thus, where continuous expression is desired throughout the cells of a plant, a constitutive promoter of the invention is utilized. In contrast, where gene expression in response to a stimulus is desired, an inducible promoter of the invention is the regulatory element of choice. When using an inducible promoter, expression of the heterologous nucleotide sequence is initiated in cells in response to a stimulus. By "stimulus" is intended a chemical, which may be applied externally or may accumulate in response to another external stimulus; a pathogen, which may, for example, induce expression as a result of invading a plant cell; or other factor such as environmental stresses, including but not limited to, drought, temperature, and salinity.

Compositions of the invention also include the nucleotide sequences for four maize PR-1 genes as set forth in SEQ ID NOs: 6, 8, 10, and 14 and the corresponding amino acid sequences for the PR-1 proteins encoded thereby as set forth in SEQ ID NOs: 7, 9, 11, and 15, respectively. These gene sequences may be assembled into a DNA construct such that the gene is operably linked to a promoter that drives expression of a coding sequence in a plant cell. Plants stably transformed with this DNA construct express, either in a constitutive or inducible manner, a PR-1 protein of the invention. Expression of this protein creates or enhances disease resistance in the transformed plant.

Fragments and variants of these native nucleotide and amino acid sequences are also encompassed by the present invention. By "fragment" is intended a portion of the nucleotide or amino acid sequence. Fragments of a promoter nucleotide sequence may retain their regulatory activity. Thus, for example, less than the entire promoter sequences disclosed herein may be utilized to drive expression of an operably linked nucleotide sequence of interest, such as a nucleotide sequence encoding a heterologous protein. It is within skill in the art to determine whether such fragments decrease expression levels or alter the nature of expression, i.e., constitutive or inducible expression. Alternatively, fragments of a promoter nucleotide sequence that are useful as hybridization probes, such as described below, generally do not retain this regulatory activity.

Nucleic acid molecules that are fragments of a promoter nucleotide sequence comprise at least 15, 20, 25, 30, 35, 40, 45, 50, 75, 100, 325, 350, 375, 400, 425, 450, 500, 550, 600, 650, 700, 800 or 900 nucleotides, or up to the number of nucleotides present in the full-length promoter nucleotide sequence disclosed herein (i.e., 957, 1218, 969, 1149, or 255 for SEQ ID NO: 1, 2, 3, 4, or 5, respectively). Fragments of a promoter sequence that retain their regulatory activity comprise at least 30, 35, 40 contiguous nucleotides, preferably at least 50 contiguous nucleotides, more preferably at least 75 contiguous nucleotides, still more preferably at least 100 contiguous nucleotides of the particular promoter nucleotide sequence disclosed herein. Preferred fragment lengths depend upon the objective and will also vary depending upon the particular promoter sequence.

The nucleotides of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335–350, and Erlich, ed. (1989) *PCR Technology* (Stockton Press, New York). Variants of these promoter fragments, such as those resulting from site-directed mutagenesis, are also encompassed by the compositions of the present invention.

With respect to PR-1 gene nucleotide sequences (i.e., for example, the sequences set forth in SEQ ID NOs: 6, 8, 10, and 14), fragments of a nucleotide sequence may encode protein fragments that retain the biological activity of the native PR-1 protein, i.e., the sequences set forth in SEQ ID NOS: 7, 9, 11, and 15, and hence enhance disease resistance when expressed in a plant. Alternatively, fragments of a coding nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the entire nucleotide sequence encoding the proteins of the invention.

A fragment of a PR-1 nucleotide sequence that encodes a biologically active portion of a PR-1 protein of the invention will encode at least 15, 25, 30, 40, 50, 75, 100, or 150 contiguous amino acids, or up to the total number of amino acids present in a full-length PR-1 protein of the invention (for example, 156, 231, 160, or 214 amino acids for SEQ ID NO: 7, 9, 11, or 15, respectively). Fragments of a PR-1 nucleotide sequence that are useful as hybridization probes for PCR primers generally need not encode a biologically active portion of a PR-1 protein.

A biologically active portion of a PR-1 protein can be prepared by isolating a portion of one of the PR-1 nucleotide sequences of the invention, expressing the encoded portion of the PR-1 protein (e.g., by recombinant expression in vitro), and assessing the activity of the encoded portion of the PR-1 protein. Nucleic acid molecules that are fragments of a PR-1 nucleotide sequence comprise at least 15, 20, 50, 75, 100, 325, 350, 375, 400, 425, 450, 500, 550, 600, 650, 700, or 800 nucleotides, or up to the number of nucleotides present in a full-length PR-1 nucleotide sequence disclosed herein (for example, 866, 973, 887, or 806 nucleotides for SEQ ID NO: 6, 8, 10, or 14, respectively).

By "variants" is intended sequences having substantial similarity with a promoter or gene nucleotide sequence disclosed herein. For nucleotide sequences, conservative variants include those sequences that, because of the degeneracy of the genetic code, encode the amino acid sequence of one of the PR-1 proteins of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a PR-1 protein of the invention. Generally, nucleotide sequence variants of the invention will have at least 40%, 50%, 60%, 70%, generally, 80%, preferably 85%, 90% to 95%, even 98% or more sequence identity to the respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. For example, amino acid sequence variants of the PR-1 proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra (eds.) *Techniques in Molecular Biology*, MacMillan Publishing Company, N.Y. (1983) and the references cited therein.

Thus, the PR-1 promoter and gene nucleotide sequences of the invention include both the naturally occurring sequences as well as mutant forms. Likewise, the proteins of the invention encompass both naturally occurring proteins as well as variations and modified forms thereof. Such variants will continue to possess the desired PR-1 promoter or antipathogenic defense protein activity. Obviously, the mutations that will be made in the DNA encoding a variant protein must not place the sequence out of reading frame and preferably will not create complementary regions that could produce secondary mRNA structure. See, for example, EP Patent Application Publication No. 75,444.

In this manner, the present invention encompasses the PR-1 proteins as well as components and fragments thereof. That is, it is recognized that component polypeptides or fragments of the proteins may be produced which retain PR-1 protein activity that enhances disease resistance in a plant. These fragments include truncated sequences, as well as N-terminal, C-terminal, internal and internally deleted amino acid sequences of the proteins.

The deletions, insertions, and substitutions of the protein sequences encompassed herein are not expected to produce radical changes in the characteristics of the PR-1 proteins. However, when it is difficult to predict the exact effect of the substitution, deletion, or insertion in advance of doing so, one skilled in the art will appreciate that the effect will be evaluated by routine screening assays. That is, the activity of the modified protein sequences can be evaluated by monitoring of the plant defense system. See, for example U.S. Pat. No. 5,614,395, herein incorporated by reference.

Thus the nucleotide sequences for the PR-1 promoters and genes of the present invention include the native forms as well as fragments and variants thereof. Similarly, the PR-1 proteins of the invention include the native forms as well as fragments and variants thereof. The variant nucleotide sequences and variant proteins will share substantial homology with their naturally occurring sequences. By "substantial homology" is intended a sequence exhibiting substantial functional and structural equivalence with the native or naturally occurring sequence. Any functional or structural differences between substantially homologous sequences do not effect the ability of the sequence to function as a promoter or as a PR-1 protein as disclosed in the present invention. Thus, for example, any sequence having substantial sequence homology with the sequence of a particular inducible promoter of the present invention will direct expression of an operably linked heterologous nucleotide sequence in response to a stimulus. Two nucleotide sequences or polypeptides are considered substantially homologous when they have at least about 50%, 60%, to 70%, generally at least about 80%, preferably at least about 85%, 90%, to 98% sequence homology. Substantially homologous sequences of the present invention include variants of the disclosed sequences such as those that result from site-directed mutagenesis, as well as synthetically derived sequences.

The nucleotide sequences of the invention can be used to isolate other homologous sequences in other plant species. Methods are readily available in the art for the hybridization of nucleic acid sequences. Promoter and coding sequences from other plants may be isolated according to well-known techniques based on their sequence homology to the PR-1 promoter and gene sequences set forth herein. In these techniques all or part of the known promoter or coding sequence is used as a probe which selectively hybridizes to other PR-1 promoter and gene sequences present in a population of cloned genomic DNA fragments or cDNA fragments (i.e., genomic or cDNA libraries) from a chosen organism.

For example, the entire PR-1 promoter or PR-1 gene sequence or portions thereof may be used as probes capable of specifically hybridizing to corresponding PR-1 promoter or PR-1 coding sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify the PR-1 promoter or coding sequences of interest from a chosen organism by the well-known process of polymerase chain reaction (PCR). This technique may be used to isolate additional promoter or coding sequences from a desired organism or as a diagnostic assay to determine the presence of PR-1 promoter or coding sequences in an organism.

Such techniques include hybridization screening of plated DNA libraries (either plaques or colonies; see, e.g., Sambrook et al. (1989) *Molecular Cloning: A Laboratory Manual* (2d ed., Cold Spring Harbor Laboratory Press, Plainview, N.Y.) and amplification by PCR using oligonucleotide primers corresponding to sequence domains conserved among the amino acid sequences (see, e.g., Innis et al., eds. (1990) *PCR Protocols, a Guide to Methods and Applications* (Academic Press, N.Y.).

For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively), to DNA encoding the PR-1 genes disclosed herein in a standard hybridization assay. See Sambrook et al. (1989) *Molecular Cloning: A Laboratory Manual* (2d ed., Cold Spring Harbor Laboratory Press, Plainview, N.Y.). In general, promoter sequences and sequences that code for the PR-1 proteins of the invention and hybridize to the sequences disclosed herein will be at least 40% to 50% homologous, 60% to 70% homologous, and even 85%, 90% to 98% homologous or more with the disclosed sequence. That is, the sequence similarity of sequences may range, sharing at least about 40% to 50%, about 60% to 70%, and even at least about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl. Math.* 2:482; by the homology alignment algorithm of Needleman et al. (1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) *Gene* 73:237–244 (1988); Higgins et al. (1989) CABIOS 5:151–153; Corpet et al. (1988) *Nucleic Acids Res.* 16:10881–90; Huang et al. (1992) *Computer Applications in the Biosciences* 8:155–65, and Person et al. (1994) *Meth. Mol. Biol.* 24:307–331; preferred computer alignment methods also include the BLASTP, BLASTN, and BLASTX algorithms (see Altschul et al. (1990) *J. Mol. Biol.* 215:403–410). Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. to about 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50, 55, or 60° C. However, nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The PR-1 proteins described herein may be used alone or in combination with other proteins or agents to protect against plant diseases and pathogens. Other plant defense proteins include those described in the copending applications both entitled "Methods for Enhancing Disease Resistance in Plants", U.S. application Ser. No. 60/076,151, filed Feb. 26, 1998, and U.S. application Ser. No. 60/092,464, filed Jul. 11, 1998, both of which are herein incorporated by reference.

The PR-1 promoter and gene nucleotide sequences disclosed herein are useful for genetic engineering of plants to express a phenotype of interest. The promoter sequences may be used to drive expression of heterologous nucleotide sequences not naturally occurring with the particular promoter sequence. Alternatively, the promoter sequences may be used to drive expression of their native, i.e., naturally occurring, PR-1 gene sequences disclosed herein. The PR-1 gene sequences, when operably linked with a promoter that drives expression in a plant cell, may be used to create or enhance disease resistance in a transformed plant.

More particularly, the nucleotide sequences for the inducible and constitutive PR-1 family of promoters disclosed in the present invention, as well as variants and fragments thereof, are useful in the genetic manipulation of any plant when assembled within a DNA construct such that the promoter sequence is operably linked with a heterologous nucleotide sequence of interest. By "operably linked" is intended the transcription or translation of the heterologous nucleotide sequence is under the influence of the promoter sequence. In this manner, the nucleotide sequences for the promoters of the invention are provided in expression cassettes along with heterologous nucleotide sequences for expression in the plant of interest.

It is recognized that the promoter sequences of the invention may also be used with their native PR-1 coding sequences to genetically engineer plants having enhanced disease resistance. A DNA construct comprising the PR-1 promoter operably linked with its native PR-1 gene may be used to transform any plant of interest to bring about a change in phenotype. Where the promoter and its native gene is naturally occurring within a plant, i.e., in maize, transformation of the plant with these operably linked sequences results in a change in phenotype, such as enhanced disease resistance, or insertion of these operably linked sequences within a different region of the chromosomes thereby altering the plant's genome.

The promoters for the PR-1 genes designated PR-1#52, PR-1#70, PR-1#81, and PR-1#83 regulate expression of an operably linked nucleotide sequence in an inducible manner. That is, expression of the operably linked nucleotide sequence in a plant cell is induced in response to a stimulus, for example in response to pathogen invasion, externally applied chemicals, or environmental stresses.

In contrast, the promoter for the PR-1 gene designated PR-1#93 is a constitutive promoter, more particularly a weak constitutive promoter. By "constitutive" is intended expression in the cells throughout a plant at most times and in most tissues. Generally, by "weak" promoter is intended a promoter that drives expression of a coding sequence at a low level. By "low level" is intended at levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts.

Thus, in one embodiment of the invention, expression cassettes will comprise a transcriptional initiation region comprising one of the promoter nucleotide sequences disclosed herein, or variants or fragments thereof, operably linked to the heterologous nucleotide sequence whose expression is to be controlled by the inducible or constitutive promoters of the invention. Such an expression cassette is provided with a plurality of restriction sites for insertion of the nucleotide sequence to be under the transcriptional regulation of the regulatory regions. The expression cassette may additionally contain selectable marker genes.

The transcriptional cassette will include in the 5'-to-3' direction of transcription, a transcriptional and translational initiation region, a heterologous nucleotide sequence of interest, and a transcriptional and translational termination region functional in plants. The termination region may be native with the transcriptional initiation region comprising one of the promoter nucleotide sequences of the present invention, may be native with the DNA sequence of interest, or may be derived from another source. Convenient termination regions are available from the Ti-plasmid of A. tumefaciens, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

The expression cassette comprising a promoter sequence of the present invention operably linked to a heterologous nucleotide sequence may also contain at least one additional nucleotide sequence for a gene to be cotransformed into the organism. Alternatively, the additional sequence(s) can be provided on another expression cassette.

Where appropriate, the heterologous nucleotide sequence whose expression is to be under the control of the promoter sequence of the present invention and any additional nucleotide sequence(s) may be optimized for increased expression in the transformed plant. That is, these nucleotide sequences can be synthesized using plant-preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak and Sarnow (1991) *Nature* 353:90–94); untranslated leader from the coat protein mRNA of alfalfa mosaic virus (AMV RNA 4) (Jobling and Gehrke (1987) *Nature* 325:622–625); tobacco mosaic virus leader (TMV) (Gallie et al. (1989) *Molecular Biology of RNA*, pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or MRNA stability can also be utilized, for example, introns, and the like.

In those instances where it is desirable to have the expressed product of the heterologous nucleotide sequence directed to a particular organelle, such as the chloroplast or mitochondrion, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

The expression cassette comprising the particular promoter sequence of the present invention operably linked to a heterologous nucleotide sequence of interest can be used to transform any plant. In this manner, genetically modified plants, plant cells, plant tissue, seed, and the like can be obtained. Transformation protocols may vary depending on the type of plant or plant cell, i.e., monocot or dicot, targeted for transformation. Suitable methods of transforming plant cells include microinjection (Crossway et al. (1986) *Biotechniques* 4:320–334), electroporation (Riggs et al. (1986) *Proc. Natl. Acad. Sci. USA* 83:5602–5606), *Agrobacterium*-mediated transformation (Hinchee et al. (1988) *Biotechnology* 6:915–921), direct gene transfer (Paszkowski et al. (1984) *EMBO J.* 3:2717–2722), and ballistic particle acceleration (see, for example, Sanford et al. U.S. Pat. No. 4,945,050; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Annual Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Klein et al. (1988) *Plant Physiol.* 91:440–444 (maize); Fromm et al. (1990) *Biotechnology* 8:833–839; Hooykaas-Van Slogteren and Hooykaas (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, ed. G. P. Chapman et al. (Longman, N.Y.), pp. 197–209 (pollen); Kaeppler et al. (1990) *Plant Cell Reports* 9:415–418; and Kaeppler et al. (1992) *Theor. Appl. Genet.* 94:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having inducible expression of the desired phenotypic characteristic identified. Two or more generations may be grown to ensure that inducible or constitutive expression of the desired phenotypic characteristic is stably maintained and inherited and then seeds harvested to ensure expression of the desired phenotypic characteristic has been achieved.

The PR-1 inducible and constitutive promoter nucleotide sequences and methods disclosed herein are useful in regulating expression of any heterologous nucleotide sequence in a host plant in order to vary the phenotype of a plant. Depending upon the PR-1 promoter used, expression may be regulated in an inducible or constitutive manner as previously described. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. patent application Ser. Nos. 08/838,763, filed Apr. 10, 1997; 08/824,379, filed Mar. 26, 1997; 08/824,382, filed Mar. 26, 1997; and U.S. Pat. No. 5,703,409; herein incorporated by reference. Another example is lysine and/or sulfur rich seed protein encoded by the soybean 2S albumin described in U.S. Ser. No. 08/618,911, filed Mar. 20, 1996, and the chymotrypsin inhibitor from barley, Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. Ser. No. 08/740,682 filed Nov. 1, 1996, and PCT/US97/20441, filed Oct. 31, 1997, the disclosures of each are incorporated herein by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference)); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example Bacillus thuringiensis toxic protein genes (U.S. Pat. Nos. 5,366,892; 5,747,450; 5,737,514; 5,723,756; 5,593,881; Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. patent application Ser. No. 08/484,815, filed Jun. 7, 1995); avirulence (avr) and disease resistance (R) genes (Jones et al. (1994) *Science* 266:789; Martin et al. (1993) *Science* 262:1432; Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins, described in U.S. Pat. application Ser. Nos. 08/838,763, filed Apr. 10, 1997; 08/824,379, filed Mar. 26, 1997; 08/824,382, filed Mar. 26, 1997; and U.S. Pat. No. 5,703,409 issued Dec. 30, 1997, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321 issued Feb. 11, 1997. Genes such as B-Ketothiolase, PHBase (polyhydroxybutyrate synthase) and acetoacetyl-CoA reductase (see Schubert et al. (1988) *J. Bacteriol.* 170:5837–5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

Thus, the heterologous nucleotide sequence operably linked to one of the inducible promoters disclosed herein may be a structural gene encoding a protein of interest. Examples of such heterologous genes include, but are not limited to, genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms.

More particularly, the constitutive and inducible promoters disclosed herein are useful in transforming plants to express an avirulence gene either constitutively or in response to pathogen invasion as disclosed in the copending applications both entitled "Methods for Enhancing Disease Resistance in Plants", U.S. application Ser. No. 60/076,151, filed Feb. 26, 1998, and U.S. application Ser. No. 60/092, 464, filed Jul. 11, 1998, both of which are herein incorporated by reference. When the constitutive promoter of the invention is used, the plant defense system is activated short of hypersensitive cell death. Thus, there is activation of the plant defense system at levels sufficient to protect from pathogen invasion. Alternatively, an inducible promoter may be used to induce the hypersensitive response. When used in this manner, induced expression of an avirulence gene causes activation of the hypersensitive plant defense system wherein the plant produces increased levels of antipathogenic factors such as PR proteins, i.e., PR-1, chitinases, β-glucanases, etc.; secondary metabolites; phytoalexins; reactive oxygen species; and the like. This hypersensitive response contains pathogen invasion, thereby enhancing disease resistance.

Alternatively, the heterologous nucleotide sequence operably linked to one of the PR-1 inducible or constitutive promoters disclosed herein may be an antisense sequence for a targeted gene. By "antisense DNA nucleotide sequence" is intended a sequence that is in inverse orientation to the 5' to 3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Thus the promoter sequences disclosed herein may be operably linked to antisense DNA sequences to reduce or inhibit expression of a native protein in the plant. Where the promoter operably linked to the antisense sequence is one of the inducible promoters of the invention, expression of a native protein is regulated in an antisense manner in response to a particular stimulus.

The nucleotide sequences for the PR-1 genes of the present invention, and variants and fragments thereof, are useful in the genetic manipulation of any plant when assembled in a DNA construct such that the gene sequence is operably linked to a promoter that drives expression of a coding sequence in a plant cell. Such a DNA construct can be used with transformation techniques, such as those described above, to create disease resistance in susceptible plant phenotypes or to enhance disease resistance in resistant plant phenotypes. Accordingly, the invention encompasses methods that are directed to protecting plants against fungal pathogens, viruses, nematodes, insects and the like.

By "disease resistance" is intended that the plants avoid the disease symptoms that are the outcome of plant-pathogen interactions. That is, pathogens are prevented from causing plant diseases and the associated disease symptoms. The method of transformation with a PR-1 gene of the invention can be utilized to protect plants from disease, particularly those diseases that are caused by plant pathogens.

Pathogens of the invention include, but are not limited to, viruses or viroids, bacteria, insects, nematodes, fungi, and the like. Viruses include tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*),

*Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidennatum, Pythium ultimum, Pythium debaryanum,* Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidmatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidenatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis O, T (Cochliobolus heterostrophus), Helminthosporium carbonum I, II & III (Cochliobolus carbonum), Exserohilum turcicum I, II & III, Helminthosporium pedicellatum, Physoderma maydis, Phyllosticta maydis, Kabatiella-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola (Glomerella graminicola), Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root knot, cyst and lesion nematodes, etc.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm, *Melanotus* spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafminer; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; *Eleodes, Conoderus,* and *Aeolus* spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; *Blissus leucopterus leucopterus,* chinch bug; *Contarinia sorghicola,* sorghum midge; *Tetranychus*

*cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips: *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis epsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

In this manner, the nucleotide sequences for the PR-1 genes are provided in expression cassettes as previously described to provide for expression in a plant of interest. Expression of the disclosed PR-1 gene sequences may be driven by any promoter that is operable within a plant cell, with the preferred promoter depending upon the desired outcome. Generally, it will be beneficial to regulate expression of the PR-1 gene using an inducible promoter, particularly a pathogen-inducible promoter such as the PR-1 inducible promoters disclosed herein. Thus any plant of interest may be transformed with an expression cassette comprising a PR-1 gene sequence disclosed herein operably linked with one of the PR-1 promoters disclosed herein, including the native PR-1 promoter for that PR-1 gene. Where expression of a PR-1 gene is driven by its native promoter, transformation of a plant with these operably linked sequences results in a plant phenotype exhibiting enhanced disease resistance. Where the transformed plant is the native plant from which the PR-1 promoter and gene sequences have been isolated, i.e., maize, the transformed plant will exhibit an altered phenotype, or have the operably linked sequences inserted at a new location within its genome.

Other inducible promoters suitable for driving expression of the PR-1 gene sequences disclosed herein include the promoters regulating expression of other pathogenesis-related proteins that are induced following infection by a pathogen; e.g., other PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116.

Of interest are promoters that are expressed locally at or near the site of pathogen infection. See, for example, Marineau et al. (1987) *Plant Mol. Biol.* 1:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Molecular and General Genetics* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; and the references cited therein. Of particular interest is the inducible promoter for the maize PRms gene, whose expression is induced by the pathogen *Fusarium moniliforme* (see, for example, Cordero et al. (1992) *Physiological and Molecular Plant Pathology* 41:189–200).

Additionally, as pathogens find entry into plants through wounds or insect damage, a wound inducible promoter may be used in the DNA constructs of the invention. Such wound inducible promoters include potato proteinase inhibitor (pin II) gene (Ryan, *Ann. Rev. Phytopath.* 28:425–449; Duan et al., *Nature Biotechnology* 14:494–498); wun1 and wun2, U.S. Pat. No. 5,428,148; win1 and win2 (Stanford et al. *Mol Gen Genet* 215:200–208); systemin (McGurl et al. *Science* 225:1570–1573); WIP1 (Rohmeier et al. *Plant Mol. Biol.* 22:783–792; Eckelkamp et al. *FEBS Letters* 323:73–76); MPI gene (Corderok et al. *Plant Journal* 6(2):141–150); and the like, herein incorporated by reference.

Alternatively, constitutive promoters can be utilized to provide continuous expression of the antipathogenic PR-1 proteins disclosed herein. Such constitutive promoters include the PR-1 promoter disclosed herein (PR-1#93, SEQ ID NO: 5), 35S promoter, ubiquitin promoter, and the like. Other constitutive promoters include, for example, U.S. Pat. Nos. 5,608,149; 5,608,144; 5,604,121; 5,569,597; 5,466,785; 5,399,680; 5,268,463; 5,608,142. See also copending U.S. application Ser. No. 60/076,075 entitled "Constitutive Maize Promoters," filed Feb. 26, 1998, herein incorporated by reference.

Tissue-specific promoters can be utilized to target enhanced disease resistance within a particular plant tissue.

Tissue-specific promoters include Yamamoto et al. (1997) *Plant J.* 12(2)255–265: Kawamata et al. (1997) *Plant Cell Physiol.* 38(7):792–803; Hansen et al. (1997) *Mol Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl Cell Differ.* 20:181–196; Orozco et al. (1993) *Plant Mol Biol.* 23 (6):1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

The expression cassette comprising a desired promoter operably linked to a nucleotide sequence for the PR-1 genes of the present invention can be used to transform any plant as described elsewhere herein. In this manner, one can obtain genetically modified plants, plant cells, plant tissue, seed, and the like that have enhanced disease resistance to a pathogen.

The following examples are offered by way of illustration and not by way of limitation.

EXPERIMENTAL

Promoter regions for five maize genes encoding pathogenesis-related class 1 (PR-1) proteins designated as PR-1#52, PR-1#70, PR-1#81, PR-1#83, PR-1#93 were isolated from maize plants and cloned. The promoter sequences for these five maize PR-1 genes are set forth in SEQ ID NOs: 1, 2, 3, 4, and 5, respectively. These genes were selected as sources of inducible promoters based on the developmental and spatial expression of their gene products. The method for promoter isolation is described below.

EXAMPLE 1

Isolation of Promoter Sequences

The procedure for promoter isolation is described in the User Manual for the Genome Walker kit sold by Clontech Laboratories, Inc., Palo Alto, Calif. Genomic DNA from maize line A63 was prepared by grinding 10-day-old seedling leaves in liquid nitrogen, and the DNA prepared as described by Chen and Dellaporta (1994) in *The Maize Handbook*, ed. Freeling and Walbot (Springer-Verlag, Berlin). RNase A was added to 10 µg/ml and then incubated at 37° C. for 1 hr. The DNA was then extracted once with phenol-chloroform, then chloroform, then ethanol precipitated and resuspended in TE (10 mM Tris pH 8.0, 1 mM EDTA). The DNA was then used exactly as described in the Genome Walker User Manual (Clontech PT3042-1 version PR68687). Briefly, the DNA was digested separately with restriction enzymes DraI, EcoRV, PvuII, ScaI, and StuI, all blunt-end cutters. The DNA was extracted with phenol, then chloroform, then ethanol precipitated. The Genome Walker adapters were ligated onto the ends of the restricted DNA. The resulting DNA is referred to as DL1–DL5, respectively.

For isolation of specific promoter regions, two nonoverlapping gene-specific primers (27–30 bp in length) were designed from the 5'end of 5 maize PR-1 cDNAs identified from sequence databases. The primers were designed to amplify the region upstream of the coding sequence, i.e., the 5' untranslated region and promoter of the chosen gene. The sequences of the primers are given below for each promoter described. The first round of PCR was performed on each DNA sample (DL 1–5) with Clontech primer API (sequence 5'-gtaatacgactcactatagggc-3'; SEQ ID NO: 16) and the gene-specific primer (gsp)1 with the following sequences:

PR-1#52:
  gsp1 (DO 18914): 5'-agc taa aca cac gac gac cct agt aga cga-3' (SEQ ID NO: 17)

PR-1#70:
  gsp1 (DO 20540): 5'-ctc cca cct cgg cgc ccg cca tta cag-3' (SEQ ID NO: 18)

PR-1#81:
  gsp1 (DO 20770): 5'-gcc agt cca tca cgg cgg cgc gga aca g-3' (SEQ ID NO: 19)

PR-1#83:
  gsp1 (DO 18912): 5'-cac gct agc ctc ggt gcc att gtt tgt tgt-3' (SEQ ID NO: 20)

PR-1#93:
  gsp1 (DO 18123): 5'-ggc tag acg act agt agg ctt cgg aaa c-3' (SEQ ID NO: 21)

PCR was performed in a model PTC-100 thermal cycler with HotBonnet from MJ Research (Watertown, Maine) using reagents supplied with the Genome Walker kit. The following cycle parameters were used: seven cycles of 94° C. for 2 sec, then 72° C. for 3 min, followed by 32 cycles of 94° C. for 2 sec, and 67° C. for 3 min. Finally, the samples were held at 67° C. for 4 min, then at 4° C. until further analysis.

As described in the User Manual, the DNA from the first round of PCR was then diluted and used as a template in a second round of PCR using the Clontech AP2 primer (sequence 5'-actatagggcacgcgtggt-3'; SEQ ID NO: 22) and gene-specific primer (gsp)2 with the following sequences:

PR-1#52:
  gsp2 (DO 18915): 5'-gca cgg cat cac ggc gac cat ggc caa-3' (SEQ ID NO: 23)

PR-1#70:
  gsp2 (DO 20352): 5'-gcg ccc gcc att aca gcc tcc tcg cgt ctt-3' (SEQ ID NO: 24)

PR-1#81:
  gsp2 (DO 20539): 5'-ggg cta gct gaa ggc tga agc aga tgg-3' (SEQ ID NO: 25)

PR-1#83:
  gsp2 (DO 18913): 5'-gac gat ggc tgc cat ggc cac agc tag gag-3' (SEQ ID NO: 26)

PR-1#93:
  gsp2 (DO 18911): 5'-cca tgg ccg cag cga ggg cag cta gcg-3' (SEQ ID NO: 27)

The cycle parameters for the second round were: 5 cycles of 94° C. for 2 sec, then 72° C. for 3 min, followed by 20 cycles of 94° C. for 2 sec, and 67° C. for 3 min and finally 4 min at 67° C., and then held at 4° C. Approximately 10 µl of each reaction were run on a 0.8% agarose gel, and bands (usually 500 bp or larger) were excised, purified with the Sephaglas BandPrep kit (Pharmacia, Piscataway, N.J.) and cloned into the TA vector pCR2.1 (Invitrogen, San Diego, Calif.). Clones were sequenced for verification.

EXAMPLE 2

Expression Data Using Promoter Sequences

A transient expression assay was used to test the cloned DNAs for promoter activity. The promoters for PR-1#52 and PR-1#83 were recloned into a GUS expression vector (FIG. 1). The ubiquitin promoter, exon 1, and intron 1 (UBI1ZM, EX1UBI1ZM, and INT1UBI1ZM) from PHP3953 were removed. The promoters were then cloned into the PstI site, 5' at bp 424 in PHP3953 and the NcoI site, 3', at bp 2430 in PHP3953. Promoter fragments were prepared for cloning into the vector by PCR with an AP1 primer to which a PstI site had been added, 5', and the appropriate gsp2 primer, to which an NcoI site had been added 3'. The PR-1#83 promoter has been cloned in front of the CRC reporter construct, as well.

Transient data from leaf sheath explants bombarded with the PR-1#83::CRC reporter construct exhibited UV-C light inducibility, indicating promoter activity. This expression was dramatically enhanced when the PR-1#83::CRC construct was cobombarded with a ubi::avrRxv construct.

EXAMPLE 3

Expression of the Maize PR-1 Genes

In order to predict where and under what conditions the PR-1 promoters may be active, we investigated the patterns of expression of the five maize PR-1 genes with Northerns. cDNA sequences for the PR-1 genes designated PR-1#52, PR-1#70, PR-1#81, PR-1#83, and PR-1#93 are set forth in SEQ ID NOs: 6, 8, 10, 12, and 14, respectively. Probable translation start codons for the four novel genes PR-1#52, PR-1#70, PR-1#81, and PR-1#93 are based on comparisons to published homologs, mostly from barley. PR-1#83 is homologous to a known maize PR-1 gene, the cDNA of which is published as GenBank Accession No. U82200.

Because the cDNA sequences showed significant homology, we made gene-specific probes using the following PCR primers, of which the reverse primers were designed to amplify fragments from the 5' ends of the representative cDNAs:
PR-1#52:
  DO 20479 5'-gct acc aca caa aaa ctt cat att tg-3' (forward primer) (SEQ ID NO: 28)
  DO 20480 5'-gca tca cgg cga cca tgg cca ac-3' (reverse primer) (SEQ ID NO: 29)
PR-1#70:
  DO 20485 5'-agg cgg cag cgg cca aga ccg gtg t-3' (forward primer) (SEQ ID NO: 30)
  DO 21053 5'-ggt gtc cct ctc gcc ctc gcc gtg g-3' (reverse primer) (SEQ ID NO: 31)
PR-1#81:
  DO 20483 5'-ccc acg cgt ccg gaa gct aca atc c-3' (forward primer) (SEQ ID NO: 32)
  DO 20484 5'-gcc acc ggc gac gcg atc tcg ag-3' (reverse primer) (SEQ ID NO: 33)
PR-1#83:
  DO 20477 5'-cat tgg act tgc act ggt gct tgc-3' (forward primer) (SEQ ID NO: 34)
  DO 20478 5'-gcg cca cga cga tgg ctg cca tg-3' (reverse primer) (SEQ ID NO: 35)
PR-1#93:
  DO 20481 5'-gaa taa cta atc aag atc gat cg-3' (forward primer) (SEQ ID NO: 36)
  DO 20482 5'-cgc cga ggc ggt cgc ggc cat c-3' (reverse primer) (SEQ ID NO: 37)

RNA was isolated from maize tissues using a guanidine thiocyanate/phenol/chloroform extraction procedure (Chomczynski and Sacchi (1987) *Anal. Biochem.* 162:156–159). Total RNA (12–30 µg/lane, depending upon the experiment) was electrophoresed in formaldehyde-agarose gels run according to Sambrook et al. (1989) *Molecular Cloning: A Laboratory Manual* (2d ed., Cold Spring Harbor Laboratory Press, Plainview, N.Y.). Gels were blotted using a Turboblotter (Schleicher and Schuell) overnight onto ZetaProbe (Bio-Rad). Gel-purified, gene-specific probes (above) were labeled by randomly-primed incorporation of $^{32}$P-ATP (see Sambrook et al. (1989) *Molecular Cloning: A Laboratory Manual* (2d ed., Cold Spring Harbor Laboratory Press, Plainview, N.Y.) catalyzed by Klenow fragment of DNA polymerase. Unincorporated label was removed from the probes with small Sepharose CL-6B (Pharmacia) spin-columns and hybridized overnight at 65° C. in roller bottles (Hybaid) in 0.5M sodium phosphate, pH 7.5, 7% (w/v) SDS. Blots were washed 2×20 min at room temperature in 40 mM sodium phosphate, pH 7.5, 5% SDS, and then 2×20 min at 65° C. in 40 mM sodium phosphate, pH 7.5, 1% SDS, then either exposed to xray film (BioMax, Kodak) or phosphoimaging screen (Molecular Dynamics).

Initial tissues analyzed for expression of the PR-1 proteins included:

dark-grown shoots (B73, which is somewhat susceptible to earmold; about 5-days-old) inoculated with *Fusarium moniliforme* spores HG11, ED42 (both very susceptible to earmold) and HT1 (resistant to earmold) silks (nonpollinated) inoculated with *F. moniliforme* spores HYII culture cells treated with chitosan, a crude preparation of chitin (from crab shells) that mimics some of the effects of fungal elicitor preparations (fungal cell walls are chitinous)

HG11, B73, and HT1 developing kernels treated with *F. moniliforme* spores leaves from families segregating lesion mimic (Les) mutations; these families have enhanced resistance to leaf blight caused by *Cochliobolus heterostrophus*.

These experiments reflect an interest in promoters that are regulated by fungal pathogens. Preliminary results of these initial analyses were as follows.

PR-1#52 mRNA was not detected in any of the above tissues. Library distribution of this cDNA, as seen in a large-scale sequencing effort, indicates that this transcript is relatively rare. The material used to generate this library can be assumed to be tissue containing a variety of transposon-induced mutations.

PR-1#70 mRNA was not detected in any of the above tissues. Library distribution of this cDNA, as seen in a large-scale sequencing effort, indicates that this clone is preferentially expressed in roots, and in leaves treated with jasmonic acid (JA) or salicylic acid (SA).

PR-1#81 mRNA accumulated dramatically (approximately 50-fold greater than the control) in HYII culture cells 12 hours after treatment with chitosan. *F. moniliforme* (Fmo) inoculation and chitooligosaccharide treatment induced strong expression of PR-1#81 in the GS3 suspension cell system at 2 hours (10- to 15-fold greater compared to controls), persisting to 12 hours. Fmo inoculation induced PR-1#81 mRNA accumulation in silks, but in an inbred-dependent manner: the transcript was detectable by 1 day in ED42 silks, and was abundant by 4 days; the transcript appeared at the level seen in ED42 at 4 days as early as 2 days in HT1; it did not accumulate to detectable levels in HG11 silks by 4 days after inoculation. Very little or no PR-1#81 message was seen in controls. Developing (liquid endosperm stage and later) kernels inoculated with Fmo spores also accumulated PR-1#81 mRNA in an inbred-dependent fashion: strong, constitutive (in controls and Fmo-treated samples) expression was seen at all time points (2 hours, 4 hours, 1 day, 4 days) in HG11; weaker, constitutive expression was seen at 2 hours and 4 hours in B73, but then Fmo-treated kernels accumulated steadily more PR-1#81 mRNA than controls, so that, by 4 days, inoculated kernels contained about 5- to 10-fold more transcript. PR-1#81 expression was strong and constitutive in dark-grown, B73 seedlings. Library distribution of the clones in this contig indicates that it is abundant and expressed in a variety of tissues, especially those experiencing stress (e.g., culture cells and insect-infested roots).

PR-1#83 mRNA was detectable in HT1 silks 2 days after Fmo treatment. Some transcript was detectable in ED42 silks 4 days after Fmo inoculation. This MRNA was very strongly expressed in Les9 and LesMT12, lesion-containing leaves; none was seen in leaves of the same age from wild-type sibs. A low, constitutive level of PR-1#83 mRNA was seen in HG11 developing kernels. Transcript was also detectable in both B73 and HT1 kernels 4 days after Fmo inoculation. PR-1#83 also appeared to be constitutively expressed in dark-grown, B73 seedlings, but much less so than PR-1#81. In addition, it accumulated in response to Fmo inoculations by 1 day, to levels about 5- to 10-fold over control. Library distribution of the clones in this contig indicates that it is found in leaf libraries, especially the TUSC and Les9 libraries.

PR-1#93 mRNA was detected only in the HG11 silks treated with Fmo spores, mildly and at 2 days after inoculation. Expression in developing kernels has not yet been examined. The pattern of expression observed for PR-1#83 in dark-grown B73 shoots matched that seen for PR-1#93. Library distribution of the clones in this contig indicates that it is also root-preferred and seen in log-phase BMS cells.

PR-1 mRNA accumulation was examined further in the following tissues:

JA-(jasmonic acid) or SA-(salicylic acid) treated leaves
UV-treated leaves
a variety of tissues from a couple of standard inbreds (HH60 and A63; e.g., roots, husks, silks, leaves, ears, tassels, etc.)
*F. moniliforme*-inoculated germinating embryos Results were as follows.

PR-1#52 expression was not induced in leaves by JA or SA treatments.

Expression was induced very weakly by UV light, as early as 24 hours after treatment, and persisted until at least 4 days after irradiation. New Northerns show PR-1#52 was mildly expressed in seedling roots, mature leaf blades, husks, and Les9 leaf tissues containing lesions.

PR-1#70 expression was not induced in leaves by JA, SA, or UV-light treatments. New Northerns show very weak expression of PR-1#70 in immature ears and husks and strong expression in cobs from maturing ears (about 23 days after pollination (dap)) and in roots from month-old plants.

PR-1#81 expression was not induced in leaves by JA and SA treatments, or immediately following UV-light treatments. Expression was mildly induced by 3 hours after UV-light treatment, about 3-fold more than that seen for PR-1#52 by 24 hours. This UV-induced expression was somewhat reduced by 4 days. PR-1#81 was constitutively expressed in kernels at 23 dap (i.e., expression wasn't induced by *Fusaria moniliforme* (Fmo) inoculation). PR-1#81 was much more strongly expressed in this tissue in HG11 kernels versus HT1 kernels. Expression was dramatically induced above a substantial background by Fmo treatment in mature HH60 embryos, which had been excised from seeds imbibed overnight and allowed to germinate, as early as 2 hours. New Northerns show that PR-1#81 is mildly expressed in seedling roots, mature leaves, husks, 23 and 40 dap kernels, and cobs from maturing ears; it is very strongly expressed in roots of month-old plants.

PR-1#83 expression was mildly induced in A63 leaves 8 hours after infiltration with SA, and mildly induced within 6 hours of a topical spray with JA. Expression was very strongly induced in leaves by UV light treatment: accumulation began by 3 hours and increased about 20- to 30-fold by 1 day. In interactions with *Cochliobous carbonum*; expression was significantly induced by 4 days into a susceptible interaction (HC-toxin-producing *C. carbonum* on Pr leaves), but only very mildly induced by 4 days in an incompatible interaction (toxin- *C. carbonum* on Pr leaves). Expression was not induced in the excised embryo system. New Northerns show that PR-1#83 was mildly expressed in roots of seedlings and month-old plants and husks; it was very strongly expressed in mature leaf blades.

PR-1#93 was constitutively expressed in green leaves, regardless of UV light, SA, or JA treatments. Its expression was seen in all tissues surveyed, including immature ears, week-old seedling leaves, seedling roots, mature blades, husks, 23 and 40 dap kernels, and silks. Expression was fairly abundant in roots from month-old plants and in cob.

Except for PR-1 accumulation in lesion mimic leaves, these observations are novel. San Segundo's reports concerning PRms show that it is induced by Fmo, but its expression is restricted to the embryos and the aleurone of germinating maize seeds (Casacuberta et al. (1992) *Mol. Gen. Genet.* 234:97–104).

EXAMPLE 4

Transformation and Regeneration of Transgenic Plants

Figure 2:
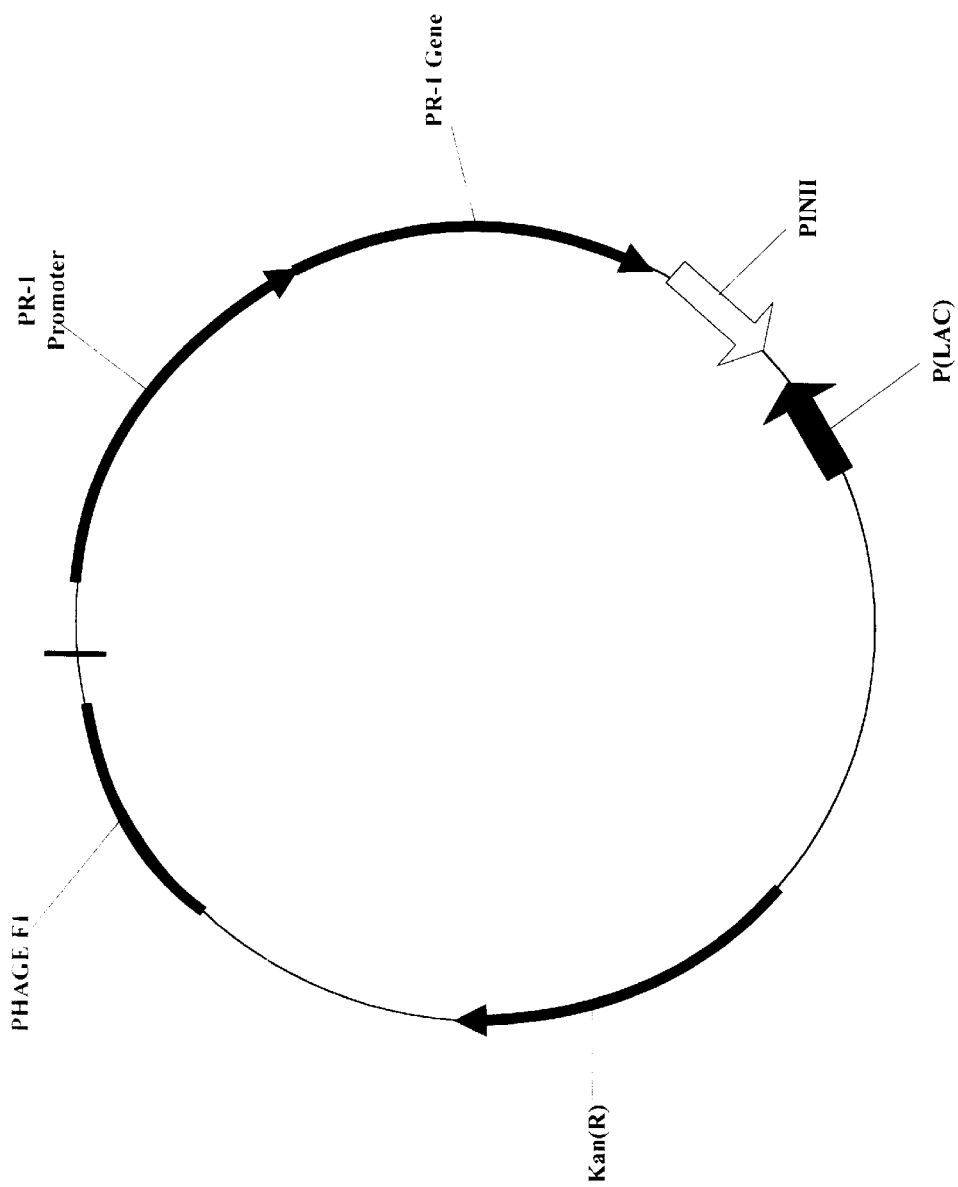
FIG. 2 provides a vector for expression of the PR-1 genes of the invention.

A maize PR-1 gene of the invention is cloned into a plant expression vector as shown in FIG. 2. The nucleotide sequence is under transcriptional control of a PR-1 inducible promoter. The selectable marker gene PAT is used.

Immature maize embryos from greenhouse donor plants are bombarded with the plasmid containing the PR-1 gene operably linked to a PR-1 inducible promoter plus a plasmid containing the selectable marker gene PAT (Wohlleben et al. (1988) *Gene* 70:25–37) that confers resistance to the herbicide Bialaphos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the PR-1 gene operably linked to a PR-1 inducible promoter is made. This plasmid DNA plus plasmid DNA containing a PAT selectable marker is precipitated onto 1.1 $\mu$m (average diameter) tungsten pellets using a $CaCl_2$ precipitation procedure as follows:

100 $\mu$l prepared tungsten particles in water
10 $\mu$l (1 $\mu$g) DNA in Tris EDTA buffer (1 $\mu$g total)
100 $\mu$l 2.5 M $CaCl_2$
10 $\mu$l 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for enhanced disease resistance.

APPENDIX

272 V

| Ingredient | Amount | Unit |
| --- | --- | --- |
| D-I H$_2$O | 950.000 | ml |
| MS Salts (GIBCO 11117-074) | 4.300 | g |
| Myo-Inositol | 0.100 | g |
| MS Vitamins Stock Solution ## | 5.000 | ml |
| Sucrose | 40.000 | g |
| Bacto-Agar @ | 6.000 | g |

Directions:

@=Add after bringing up to volume

Dissolve ingredients in polished D-I H$_2$O in sequence

Adjust to pH 5.6

Bring up to volume with polished D-I H$_2$O after adjusting pH

Sterilize and cool to 60° C.

=Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions.

Thiamine.HCL & Pyridoxine.HCL are in Dark Desiccator. Store for one month, unless contamination or precipitation occurs, then make fresh stock.

Total Volume (L)=1.00

288 J

| Ingredient | Amount | Unit |
| --- | --- | --- |
| D-I H$_2$O | 950.000 | ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| .1 mM Abscisic Acid | 1.000 | ml |
| Bialaphos 1 mg/ml # | 3.000 | ml |

Directions:

@=Add after bringing up to volume

Dissolve ingredients in polished D-I H$_2$O in sequence

Adjust to pH 5.6

Bring up to volume with polished D-I H$_2$O after adjusting pH

Sterilize and cool to 60° C.

Add 3.5 g/L of Gelrite for cell biology.

=Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions.

Thiamine.HCL & Pyridoxine.HCL are in Dark Desiccator. Store for one month, unless contamination or precipitation occurs, then make fresh stock.

Total Volume (L)=1.00

560 R

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:

@=Add after bringing up to volume

=Add after sterilizing and cooling to temp.

Dissolve ingredients in D-I H$_2$O in sequence

Adjust to pH 5.8 with KOH

Bring up to volume with D-I H$_2$O

Sterilize and cool to room temp.

Total Volume (L)=1.00

560 Y

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511 | 1.000 | ml |
| Thiamine.HCL 0.4 mg/ml | 1.250 | ml |
| Sucrose | 120.000 | g |
| 2,4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:
@=Add after bringing up to volume
=Add after sterilizing and cooling to temp.
Dissolve ingredients in D-I H$_2$O in sequence
Adjust to pH 5.8 with KOH
Bring up to volume with D-I H$_2$O
Sterilize and cool to room temp.
Autoclave less time because of increased sucrose
Total Volume (L)=1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated promoter comprising a nucleotide sequence that initiates transcription in a plant cell, wherein said nucleotide sequence is selected from the group consisting of:
   a) a nucleotide sequence comprising the sequence set forth in SEQ ID NO: 3 or 4; and
   b) a nucleotide sequence comprising the plant promoter sequence deposited in the plasmid designated as ATCC Accession No. 207139 or 207131.

2. A DNA construct comprising the promoter of claim 1 operably linked to a heterologous nucleotide sequence of interest.

3. An expression cassette comprising the DNA construct of claim 2.

4. A host cell having stably incorporated in its genome the DNA construct of claim 2.

5. A method for driving expression of a heterologous nucleotide sequence in a plant, said method comprising the steps of:
   a) transforming a plant cell with an expression cassette comprising the heterologous nucleotide sequence operably linked to a promoter that initiates transcription in a plant cell, wherein said promoter is selected from the group consisting of:
      i) a nucleotide sequence comprising the sequence set forth in SEQ ID NO: 3 or 4; and
      ii) a nucleotide sequence comprising the plant promoter sequence deposited in the plasmid designated as ATCC Accession No. 207139 or 207131; and
   b) regenerating a stably transformed plant from said plant cell.

6. The method of claim 5, wherein said plant is a monocot.

7. The method of claim 6, wherein said monocot is maize.

8. The method of claim 5, wherein said plant is a dicot.

9. A plant cell transformed with a DNA construct comprising a heterologous nucleotide sequence operably linked to a promoter that initiates transcription in said plant cell, wherein said promoter comprises a nucleotide sequence selected from the group consisting of:

a) a nucleotide sequence comprising the sequence set forth in SEQ ID NO: 3 or 4; and b) a nucleotide sequence comprising the plant promoter sequence deposited in the plasmid designated as ATCC Accession No. 207139 or 207131.

10. The plant cell of claim 9, wherein said plant cell is from a monocot.

11. The plant cell of claim 10, wherein said monocot is maize.

12. The plant cell of claim 9, wherein said plant cell is from a dicot.

13. A plant stably transformed with a DNA construct comprising a heterologous nucleotide sequence operably linked to a promoter that initiates transcription in a plant cell, wherein said promoter comprises a nucleotide sequence selected from the group consisting of:

a) a nucleotide sequence comprising the sequence set forth in SEQ ID NO: 3 or 4; and b) a nucleotide sequence comprising the plant promoter sequence deposited in the plasmid designated as ATCC Accession No. 207139 or 207131.

14. The plant of claim 13, wherein said plant is a monocot.

15. The plant of claim 14, wherein said monocot is maize.

16. The plant of claim 13, wherein said plant is a dicot.

17. Seed of the plant of any one of claims 13–16.

* * * * *

UNITED STATES PATENT AND TRADEMARK OFFICE
CERTIFICATE OF CORRECTION

PATENT NO.    : 6,429,362 B1                                      Page 1 of 1
DATED         : August 6, 2002
INVENTOR(S)   : Virginia C. Crane It is certified that error appears in the above-identified patent and that said Letters Patent is hereby corrected as shown below:

<u>Title page,</u>
Item [57], ABSTRACT, should be replaced with the ABSTRACT listed below:

```
The present invention provides compositions and methods for
regulating expression of heterologous nucleotide sequences in
a plant.  Compositions are novel nucleotide sequences for
inducible and constitutive promoters isolated from a family
of maize genes encoding pathogenesis-related (PR-1) proteins,
nucleotide sequences for these maize PR-1 genes, and amino
acid sequences for the PR-1 proteins encoded thereby.  Methods
for regulating expression of a heterologous nucleotide sequence
in a plant in an inducible or constitutive manner are provided,
more particularly regulating expression of a PR-1 gene to
enhance disease resistance in a plant.  The methods comprise
transforming a plant cell to comprise a heterologous nucletoide
sequence or PR-1 gene operably linked to one of the inducible
or constitutive promoters of the present invention and regenerating
a stably transformed plant from the transformed plant cell.
Transformed plants and seeds having enhanced disease resistance
are also provided.
```

Signed and Sealed this

Twenty-fifth Day of March, 2003

JAMES E. ROGAN
*Director of the United States Patent and Trademark Office*